US008980603B2

(12) United States Patent
Tannous et al.

(10) Patent No.: US 8,980,603 B2
(45) Date of Patent: Mar. 17, 2015

(54) *GAUSSIA* LUCIFERASE VARIANT FOR HIGH-THROUGHPUT SCREENING

(75) Inventors: Bakhos A. Tannous, Malden, MA (US); Casey Maguire, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 350 days.

(21) Appl. No.: 13/381,788

(22) PCT Filed: Jun. 30, 2010

(86) PCT No.: PCT/US2010/040660
§ 371 (c)(1),
(2), (4) Date: Feb. 6, 2012

(87) PCT Pub. No.: WO2011/002924
PCT Pub. Date: Jan. 6, 2011

(65) Prior Publication Data
US 2012/0122182 A1    May 17, 2012

Related U.S. Application Data

(60) Provisional application No. 61/221,673, filed on Jun. 30, 2009.

(51) Int. Cl.
*C12N 9/00* (2006.01)
*C12N 9/02* (2006.01)
*C12N 1/20* (2006.01)
*C12N 15/00* (2006.01)
*C07H 21/04* (2006.01)

(52) U.S. Cl.
CPC ................ *C12Y 113/12005* (2013.01); *G01N 2333/90241* (2013.01); *C07K 2319/00* (2013.01); *C12N 9/0069* (2013.01)
USPC ..... 435/189; 435/183; 435/252.3; 435/320.1; 536/23.2

(58) Field of Classification Search
None
See application file for complete search history.

(56) References Cited

U.S. PATENT DOCUMENTS

| 6,232,107 B1 | 5/2001 | Bryan et al. |
| 6,436,682 B1 | 8/2002 | Bryan et al. |
| 7,109,315 B2 | 9/2006 | Bryan et al. |

FOREIGN PATENT DOCUMENTS

WO    0131028 A2    5/2001

OTHER PUBLICATIONS

Accession AAG54095. Oct. 18, 2005.*
Badr, C.E. et al. "A Nightly Sensitive Assay for Monitoring the Secretory Pathway and ER Stress," PLoS ONE Issue 6, e571 (2007).
Bhaumik, S. et al. "Optical imaging of *Renilla* luciferase reporter gene expression in living mice," Proc Natl Acad Sci U S A 99: 377-382 (2002).
Contag, C.H. et al. "It's Not Just About Anatomy: In Vivo Bioluminescence Imaging as an Eyepiece into Biology," J Magn Reson Imaging 16:378-387 (2002).
Davis, A.L. "Improved Red-emitting Firefly Luciferase Mutant for Biotechnical Applications," Chemistry Honors Papers. May 2009, Paper 5 pp. 1-34 (http://digitalcommons.conncoll.edu/chemhp/5).
de Wet, J.R. et al. "Cloning of firefly luciferease cDNA and the expression of active luciferase in *Escherichia coli*," Proc Natl Acad Sci U S A 82: 7870-7873 (1985).
GenBank Accession No. AY015993: *Gaussia* princepts (T. Scott, 1894) luciferase mRNA, complete cds. Oct. 18, 2005.
GenBank Accession No. FJ010198: Expression vector pKLAC1-Gluc, complete sequence. Oct. 15, 2008.
Greer, L.F. "Imaging of light emission from the expression of luciferases in living cells and organisms: a review," Luminescence 17: 43-74 (2002).
Hattori, N. et al. "Mutant Luciferase Enzymes from Fireflies with Increased Resistance to Benzalkonium Chloride." Biosci. Biotechnol. Biochem. 66(12):2587-2593 (2002).
Hewett, J.W. et al. "Mutant torsinA interferes with protein processing through the secretory pathway in SYT1 dystonia cells," Proc Natl Acad Sci U S A 104, 7271-7276 (2007).
Ketteler, R. et al. "A pathway sensor for genome-wide screens of intracellular proteolytic cleavage," Genome Biol 9, R64 (2008).
Koksharov, M.I. et al. "Random Mutagenesis of *Luciola mingrelica* Firefly Luciferase. Mutant Enzymes with Bioluminescence Spectra Showing Low pH Sensitivity." Biochemistry (Moscow). 73(8):862-869 (2008).
Lee, J.Y et al. "Development of a Dual-Luciferase Reporter System for In Vivo Visualization of MicroRNA Biogenesis and Post-transcriptional Regulation," J Nucl Med 49: 285-294 (2008).
Maguire, C.A. et al. "*Gaussia* luciferase variant for high-throughput functional screening applications," Analytical Chemistry 81(16):7102-7106 (2009).
Massoud, T.F. et al. "Molecular imaging in living subjects: seeing fundamental biological processes in a new light," Genes Dev 17: 545-580 (2003).
Remy, I. et al. "A highly sensitive protein-protein interaction assay based on *Gaussia* luciferase," Nat Methods 3: 977-979 (2006).
Santos, E.B. et al. Sensitive in vivo imaging of T cells using a membrane-bound *Gaussia* princeps luciferase, J. Nat Med 15: 338-344 (2009).
Stemmer, W.P. "Rapid evolution of a protein in vitro by DNA shuffling," Nature 370, 389-391 (1994).

(Continued)

*Primary Examiner* — Christian Fronda
(74) *Attorney, Agent, or Firm* — Shayne Y. Huff; David S. Resnick; Nixon Peabody LLP

(57) ABSTRACT

Described herein is a variant of wild type Gaussia luciferase that catalyzes glow-type emission kinetics suited for high-throughput functional screening applications. Polypeptides, functional fragments, variants, and nucleic acids that encode the enhanced luciferase are further described. One such polypeptide corresponds to wild type Gaussia luciferase with a substitution mutation of I for M at position 43 of the mature peptide. Methods of use, assay systems and kits that contain the polypeptides and/or nucleic acids are further described.

20 Claims, 8 Drawing Sheets

(56) References Cited

OTHER PUBLICATIONS

Suzuki, T. "Real-time bioluminescence imaging of a protein secretory pathway in living mammalian cells using *Gaussia* luciferase," FEBS Lett 581, 4551-4556 (2007).

Tannous, B.A. et al. "Codon-Optimized Gaussia Luciferase cDNA for Mammalian Gene Expression in Culture and in Vivo," Mol Ther 11: 435-443 (2005).

Verhaegen, M. et al. "Recombinant *Gaussia* Luciferase. Overexpression, Purification, and Analytical Application of a Bioluminescent Reporter for DNA Hybridization," Anal Chem 74: 4378-4385 (2002).

Wiles, S. et al. "Alternative Luciferase for Monitoring Bacterial Cells under Adverse Conditions," Appl Environ Microbiol 71: 3427-3432 (2005).

Wurdinger, T. "A secreted luciferase for ex vivo monitoring of in vivo processes," et al. Nat Methods 5:171-173 (2008).

\* cited by examiner

Figure 3

```
                                                                    Section 1
            (1)  1         10         20         30         40           58
WT Gluc    (1)  ░░░░░░░░░░░░░░░░░░░░░░░░░░░░░░░░░░░░░░░░░░░░░░░░░░░░░░░░
GlucM43I   (1)  ░░░░░░░░░░░░░░░░░░░░░░░░░░░░░░░░░░░░░░░░░░░■░░░░░░░░░░░░
Consensus  (1)  KPTENNEDFNIVAVASNFATTDLDADRGKLPGKKLPLEVLKEIEANARRAGCTRGCLI
                                                                    Section 2
            (59) 59        70         80         90        100          116
WT Gluc    (59)  ░░░░░░░░░░░░░░░░░░░░░░░░░░░░░░░░░░░░░░░░░░░░░░░░░░░░░░
GlucM43I   (59)  ░░░░░░░░░░░░░░░░░░░░░░░░░░░░░░░░░░░░░░░░░░░░░░░░░░░░░░
Consensus  (59) CLSHIKCTPKMKKFIPGRCHTYEGDKESAQGGIGEAIVDIPEISGFKDLEPMEQFIAQ
                                                                    Section 3
            (117) 117       130        140        150          168
WT Gluc   (117)  ░░░░░░░░░░░░░░░░░░░░░░░░░░░░░░░░░░░░░░░░░░░░░░░░░░
GlucM43I  (117)  ░░░░░░░░░░░░░░░░░░░░░░░░░░░░░░░░░░░░░░░░░░░░░░░░░░
Consensus (117) VDLCVDCTTGCLKGLANVQCSDLKKWLPQRCATFASKIQGQVDKIKGAGGD
```

Figure 6
6A
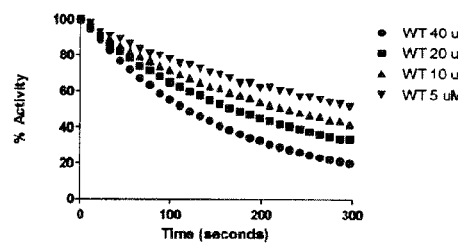
6B
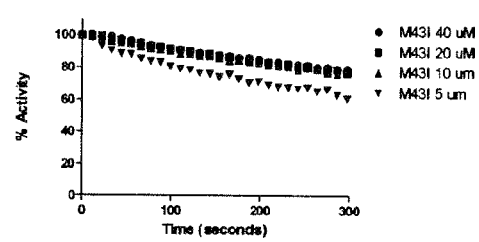

Figure 7
7A
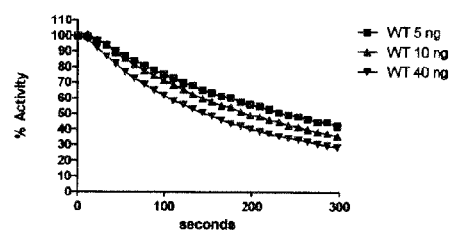
7B
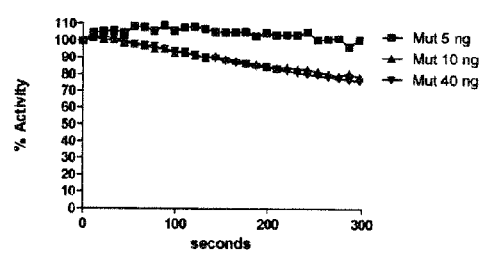

GAUSSIA LUCIFERASE VARIANT FOR HIGH-THROUGHPUT SCREENING

CROSS REFERENCE

RELATED APPLICATIONS

This application is a 35 U.S.C. 371 National Stage entry of International Application No. PCT/US2010/040660, filed Jun. 30, 2010, which designates the United States, and which claims the benefit under 35 U.S.C. 119(e) of U.S. Provisional Patent Application Ser. No: 61/221,673, filed Jun. 30, 2009, the contents of each of which are incorporated herein by reference in their entirety.

GOVERNMENT SUPPORT

This invention was supported by the National Institutes for Health (NIH) and National Institute of Neurological Disorders and Stroke (NINDS) Grant No. 1R21NS061051 and 5 T32 CA073479-09, and the Government of the United States has certain rights thereto.

FIELD OF THE INVENTION

The present invention relates to the field of materials and methods for the identification and assessment of biological systems. More particularly, the invention relates to a system for real-time analysis of biological systems using a secreted luciferase.

BACKGROUND

Luciferases catalyze light emission in the presence of their substrates, luciferins, and this property has made them a staple in multiple basic scientific research applications ranging from quantitative analysis of promoter activity and cell viability and proliferation in cultured cells to non-invasive bioluminescence imaging of biological processes such as cell tracking, tumor growth kinetics and response to therapy in vivo.[1-3] There are different types of luciferases that occur in species including beetles, bacteria, worms, fungi, and squid with several of them cloned and tested for molecular biology research.[4,5] Each of these luciferases has different characteristics which makes them attractive for certain applications but not optimal for others. For high-throughput applications, an optimal luciferase would display the following characteristics: (1) enzyme stability over a variety of conditions; (2) high light output for increased sensitivity; (3) non-invasive monitoring of enzymatic activity at different time points in real-time; and (4) the catalysis of stable light emission for minimal variability between thousands of screened wells.

The marine copepod, Gaussia princeps, secretes a luciferase (Gluc) which possesses all but the fourth characteristic. In recent years, the cloned cDNA of Gluc has been shown to be the preferred luciferase type for many different biological applications.[6-13] Gluc is the smallest luciferase cloned (18 kDa) with several advantages over other commonly used reporters: Gluc is over 2,000-fold more sensitive than firefly (Fluc) or *Renilla* (Rluc) luciferases and 20,000-fold more sensitive than the secreted alkaline phosphatase;[6,14] Gluc is naturally secreted and therefore monitoring of biological processes can be accomplished in real-time by measuring enzymatic activity in aliquots of conditioned medium in cultured cells at different time points keeping the cells intact for confirmation analysis making it useful for studying assay kinetics;[6,15] it is stable over a wide pH range and in the presence of reactive compounds;[14,16] in vivo, Gluc can be detected in blood or urine making it a sensitive ex-vivo tool for monitoring of in vivo processes.[13] One limitation of Gluc for high-throughput assays is the rapid decay of its bioluminescence reaction and therefore a luminometer with a built-in injector is required, making the assay time consuming.[14]

SUMMARY

Aspects of the present invention relate to the identification of a variant of wild type Gaussia luciferase that, in the presence of a substrate (e.g, coelenterazine) and a detergent (e.g., Triton X-100), catalyzes glow-type emission kinetics suited for high-throughput functional screening applications. As such, aspects of the invention relate to polypeptides that make up the luciferase and nucleic acid sequences which encode them.

One aspect of the invention relates to an isolated nucleic acid fragment comprising a sequence of nucleotides encoding a polypeptide comprising the amino acid sequence set forth in SEQ ID NO: 1, with a substitution mutation at the position 43, or a functional fragment thereof, wherein the polypeptide catalyzes a stable light emission output in the presence of a detergent, as compared to a comparable polypeptide which has a Methionine at position 43.

In one embodiment, the detergent is Triton X-100, present in the amount of 0.1%.

In one embodiment, the substitution mutation is a conservative mutation.

In one embodiment, the conservative substitution mutation is the substitution of Tyrosine, Leucine and Isoleucine.

In one embodiment, the substitution mutation is an Isoleucine for Methionine.

In one embodiment, the nucleotide sequence corresponds to nucleotides 52-555 of SEQ ID NO: 4, with a nucleotide change in codon 60 that results in an amino acid substitution mutation.

In one embodiment, the nucleotide sequence corresponds to nucleotides 52-555 of SEQ ID NO: 5, with a nucleotide change in codon 60 that results in an amino acid substitution mutation.

In one embodiment, of the above stated embodiments, the substitution mutation is a conservative substitution mutation for Methionine.

In one embodiment, the conservative substitution mutation is a substitution of Tyrosine, Leucine or Isoleucine.

In one embodiment, the conservative substitution mutation is a substitution of Isoleucine.

In one embodiment, of the above stated embodiments, the isolated nucleic acid fragment further comprises and is operatively linked to a nucleic acid fragment encoding an additional functional polypeptide sequence.

In one embodiment, the additional functional polypeptide sequence is selected from the group consisting of an affinity tag, an enzyme, and a visible marker.

In one embodiment, of the above stated embodiment, the nucleic acid fragment further comprises and is operatively linked to a regulatory response element.

Another aspect of the invention relates to a plasmid comprising the nucleic acid fragment of the various embodiments described above.

Another aspect of the invention relates to an expression vector comprising the nucleic acid fragment of the various embodiments described above.

In one embodiment, the expression vector or the plasmid further comprises a polylinker region for in-frame sub-cloning of a nucleic acid encoding a second polypeptide sequence.

Another aspect of the invention relates to a cell comprising the nucleic acid fragment of the various embodiments described above.

Another aspect of the invention relates to a cell comprising the expression vector of the various embodiments described above.

Another aspect of the invention relates to a transgenic organism comprising the nucleic acid fragment of the various embodiments described above.

Another aspect of the invention relates to a a polypeptide comprising the amino acid sequence set forth in SEQ ID NO: 1, with a substitution mutation at the position 43, or a functional fragment thereof, wherein the polypeptide catalyzes a stable light emission output in the presence of a detergent, as compared to a comparable polypeptide which has a methionine at position 43.

In one embodiment, the substitution mutation is a conservative mutation.

In one embodiment, the conservative substitution mutation is the substitution of Tyrosine, Leucine and Isoleucine.

In one embodiment, the substitution mutation is an Isoleucine for Methionine.

In one embodiment, the polypeptide or functional fragment thereof described above, further comprises an additional functional polypeptide sequence.

In one embodiment, the additional functional polypeptide sequence is selected from the
group consisting of an affinity tag, an enzyme, and a visible marker.

In one embodiment of the embodiments described above, the polypeptide or functional
fragment is substantially pure.

In one embodiment, of the embodiments described above, the detergent is Triton X-100.

Another aspect of the invention relates to an assay system comprising a polypeptide comprising the amino acid sequence set forth in SEQ ID NO: 1, with a substitution mutation at the position 43, or a functional variant or functional fragment thereof, wherein the polypeptide catalyzes a stable light emission output in the presence of a detergent, as compared to a comparable polypeptide which has a Methionine at position 43.

Another aspect of the invention relates to an assay system comprising a nucleic acid fragment described in the various above embodiments.

Another aspect of the invention relates to an assay system comprising a host cell comprising a nucleic acid fragment described in the various above embodiments.

In one embodiment of the assay systems described above, the assay system is a high-throughput assay.

Another aspect of the invention relates to a method of detecting modulation of a regulatory element, comprising: providing a nucleic acid encoding the polypeptide or functional fragment thereof, described in the various above embodiments, operatively linked to the regulatory element under conditions suitable for expression; and detecting modulation of the expression of the polypeptide in a bioluminescence assay system wherein the detected modulation indicates like modulation of the regulatory element.

Another aspect of the invention relates to a method of detecting a molecule in a biological assay, comprising: providing the molecule in the form of a linkage to the polypeptide or functional fragment thereof, described in the various above embodiments, and detecting the presence of the polypeptide with a bioluminescence assay, to thereby detect the presence of the molecule.

Another aspect of the invention relates to a polypeptide comprising the amino acid sequence set forth in SEQ ID NO: 1, with a substitution mutation at the position 43, or a functional variant or functional fragment thereof, wherein the polypeptide catalyzes a stable light emission output in the presence of a detergent, as compared to a comparable polypeptide which has a Methionine at position 43.

Another aspect of the invention relates to a method of detecting modulation of a regulatory element, comprising: providing a nucleic acid encoding the polypeptide or functional variant or fragment thereof, described in the various above embodiments, operatively linked to the regulatory element under conditions suitable for expression; and detecting modulation of the expression of the polypeptide in a bioluminescence assay system wherein the detected modulation indicates like modulation of the regulatory element.

Another aspect of the invention relates to a method of detecting a molecule in a biological assay, comprising: providing the molecule in the form of a linkage to the polypeptide or functional variant or fragment thereof, of described in the various above embodiments, and detecting the presence of the polypeptide with a bioluminescence assay, to thereby detect the presence of the molecule.

Another aspect of the invention relates to a kit comprising the expression vector described in the various above embodiments, and instructions.

Definitions

As used herein, a "biological sample" refers to a sample of biological material obtained from a patient, preferably a human patient, including a tissue, a tissue sample, a cell sample (e.g., a tissue biopsy, such as, an aspiration biopsy, a brush biopsy, a surface biopsy, a needle biopsy, a punch biopsy, an excision biopsy, an open biopsy, an incision biopsy or an endoscopic biopsy), and a tumor sample. Biological samples can also be biological fluid samples. These include semen, urine, blood, serum, saliva, cerebrospinal fluid, nipple aspirates, and supernatant from cell lysate.

As the term is used herein, a "bioluminescence-generating system" refers to the components that are necessary and sufficient to generate bioluminescence. Thus a bioluminescence generating system refers to any set of reagents that, under appropriate reaction conditions, yield bioluminescence. Appropriate reaction conditions refers to the conditions necessary for a bioluminescence reaction to occur, such as pH, salt concentrations and temperature, as well as containing the appropriate components. Necessary components include, without limitation, a luciferase, substrate (e.g., luciferin, or other suitable substrates) any necessary co-factors or activators, solvents and other reagents that may be required to complete a bioluminescent reaction.

As the term is used herein, a "bioluminescence assay system" refers to an assay for the quantitative or qualitative detection of the luciferase protein by its enzymatic activity. In such an assay system, suitable reagents and appropriate controls, positive and negative, are used to determine the presence (quantitative or qualitative) of a luciferase protein in one or more samples. Such systems are typically utilized in the detection of an activity which increases or decreases the presence of a functional luciferase protein. For example, a reporter assay based on the expression of luciferase as a reporter protein, qualitatively provide information on the activity of regulatory elements linked to the nucleic acids encoding the luciferase in an expression system. In such assays, by utilizing the appropriate controls, it is not necessary to quantitatively determine the amount of luciferase, but rather determination of the relative amounts, through the quantitation of the luminescent product produced by the luciferase enzymatic activity, provides qualitative information regarding an appropriately linked regulatory element. Assays based on luciferase protein function (inhibiting or activating the function of the expressed protein) can also be envisioned, and are also encompassed by the present invention.

As used herein, bioluminescence substrate refers to the compound that is oxidized in the presence of a luciferase, and any necessary activators, and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, Cypridina (also known as Vargula), luciferin (coelenterazine), bacterial luciferin, as well as synthetic analogs of these substrates or other compounds that are oxidized in the presence of a luciferase in a reaction the produces bioluminescence.

As the term is used herein, a substantially pure polypeptide or protein refers to the fact that the polypeptide is substantially separate or otherwise isolated from other components (e.g., of the cell from which it was produced). Other components include, without limitation, other cellular components such as other proteins, nucleic acids, polysaccharides, etc. For some uses, a crude extract is sufficient. Generally substantially pure refers to a sample that is sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. Substantially pure refers to a sample wherein Examples of appropriate sample forms are a solution, a lyophilized powder, a gel, etc. in one embodiment, at least about 50%, 60%, 70%, 80% or 90% of sample components (e.g., by weight) is the polypeptide or protein.

Functional fragment refers to a fragment of a luciferase polypeptide of the present invention which retains catalytic activity in a bioluminescence reaction, and demonstrates stable light emission output as compared to a comparable wild type fragment, as described herein. In one embodiment, the functional fragment is secreted by the cell in which it is expressed.

Functional variant refers to a polypeptide of the present invention containing one or more amino acid substitutions, insertions or deletions, which retains catalytic activity in a bioluminescence reaction, and demonstrates stable light emission output as compared to a comparable wild type polypeptide, as described herein. In one embodiment, the functional variant is secreted by the cell in which it is expressed.

The term "conjugate" refers to the attachment of two or more molecules joined together to form one entity, as in the attachment of a polypeptide of the present invention with another molecule. The molecules (e.g, proteins) may attach together by linkers, chemical modification, peptide linkers, chemical linkers, covalent or non-covalent bonds, or protein fusion or by any means known to one skilled in the art. The joining may be permanent or reversible. In some embodiments, several linkers may be included in order to take advantage of desired properties of each linker and each molecule in the conjugate. Flexible linkers and linkers that increase the solubility of the conjugates are contemplated for use alone or with other linkers are incorporated herein. Peptide linkers may be linked by expressing DNA encoding the linker to one or more proteins in the conjugate. Linkers may be acid cleavable, photocleavable and heat sensitive linkers.

The term "fusion protein" refers to a recombinant protein of two or more typically independent polypeptide sequences. Fusion proteins can be produced, for example, by a nucleic acid sequence encoding one protein is joined to the nucleic acid encoding another protein such that they constitute a single open-reading frame that can be translated in the cells into a single protein harboring all the intended polypeptide sequences. The order of arrangement of the polypeptide sequences can vary. In one embodiment, function of all linked polypeptide sequences is preserved. In another embodiment, the function of one or more of the polypeptide sequences is masked. A masked function may be designed for revealing upon exposure to the appropriate stimuli such as chemical cleavage, phosphorylation, binding, etc. of the fusion protein.

As used herein, operatively linked refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, eg., Kozak (1991) J. Biol. Chem. 266:19867-19870) can be inserted immediately 5' of the start codon and may enhance expression. The desirability of (or need for) such modification may be empirically determined.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" and "regulatory response elements", and refers to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence can be nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, operate sequences to control transcription, mRNA ribosomal binding sites, and sequences to control the termination of transcription and/or translation.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

Nucleic acids that are operatively linked to a regulatory sequence, will generally also be linked to a promoter. As such, the term operatively linked, in reference to a regulatory sequence, is intended to refer to the presence of other necessary nucleic acid sequences, such as a promoter, which are necessary for transcription and translation of the nucleic acid sequences.

BRIEF DESCRIPTION OF THE DRAWINGS

FIG. 3 shows the amino acid composition of the GlucM43I variant (SEQ ID NO: 2), and the wild type Gluc protein (SEQ ID NO: 1), and the consensus sequence (SEQ ID NO: 2). Alignment of the wt Gluc with GlucM43I sequence was performed using Vector NTI AlignX. The signal peptide is not shown.

FIG. 6A-FIG. 6B is two graphs showing data from light emission kinetics with variation in coelenterazine concentrations. A) Kinetics of light decay using 10 ng of wt Gluc using different amounts of coelenterazine. B) Kinetics of light decay using 10 ng of GlucM43I using different amounts of coelenterazine.

FIG. 7A-FIG. 7B is two graphs showing data from kinetics of light decay with varying amounts of Gluc or GlucM43I. Different amounts of wt Gluc (A) or GlucM43I (B) in 50 µl of 30 mM Tris pH 8.0, 0.1% Triton-X-100 were mixed with an equal volume of 20 µM coelenterazine diluted in 1×PBS, 5 mM NaCl and reaction kinetics was monitored over 5 minutes.

DETAILED DESCRIPTION

Figure 1:
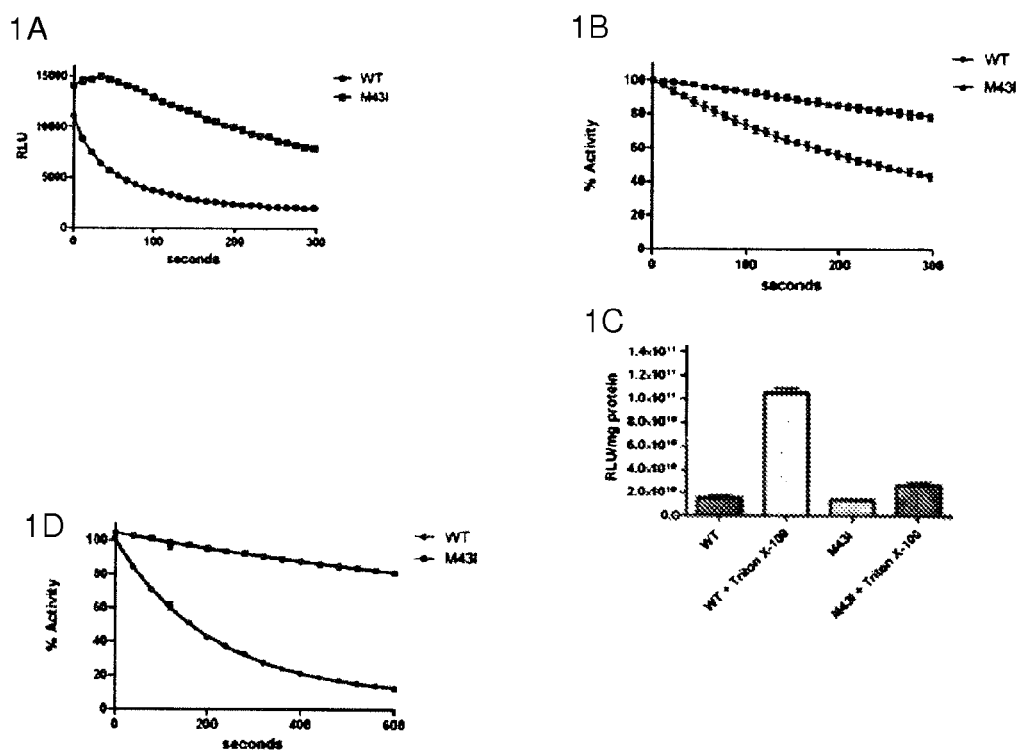
FIG. 1A-FIG. 1D is data that shows the GlucM43I variant catalyzes glow-type luminescence reaction. (A) Small-scale cultures of bacteria transformed with plasmids encoding wt Gluc or GlucM43I variant were lysed using 30 mM Tris-HCl pH 8.0, 2 mM EDTA, 0.1% Triton X-100, mixed with coelenterazine, and a five-minute kinetic assay for light emission was performed. Relative Light Units (RLU). Wt Gluc and GlucM43I were expressed as 6His-tagged proteins and purified on a $Ni^{2+}$ column. (B) Kinetic analysis of purified Gluc and GlucM43I in 30 mM Tris, pH 8.0, 0.1% Triton X-100 as quantified using the luminometer (B). (C) Specific activity of wt Gluc and GlucM43I variant analyzed from two independent purifications after addition of 50 µl coelenterazine diluted in 30 mM Tris-HCl pH 8.0. (D) Kinetic analysis of Gluc and GlucM43I variant expressed in mammalian cells. 293T cells were transiently transfected with a mammalian expression vector encoding either wt Gluc or GlucM43I variant. Forty-eight h post-transfection, Gluc luminescence kinetics (over 10 min) were analyzed in five µl aliquots of the conditioned media after addition of 95 µl 40 µM coelenterazine diluted in 30 mM Tris pH 8.0 with 5 mM NaCl and 0.1% Triton X-100 using a luminometer. Results presented as % in which the RLU from the first reading is set to 100%. All data shown are representative of three independent experiments. Error bars represent standard deviation.

Aspects of the present invention relate to the identification of a variant of wild type Gaussia luciferase that, in the presence of a substrate (e.g, coelenterazine) and a detergent (e.g., Triton X-100), catalyzes glow-type emission kinetics suited for high-throughput functional screening applications. The luciferase protein contains an amino acid mutation that enhances the stability of the light emission output, and is referred to herein as an enhanced luciferase or an enhanced Gaussia luciferase. The enhanced Gaussia luciferase catalyzes a stable light emission output in the presence of a substrate and a detergent, as compared to the comparable wild type polypeptide, under the same reaction conditions. As such, one aspect of the present invention relates to such an enhanced Gaussia luciferase. The enhanced Gaussia luciferase of the present invention can be identified based on its amino acid homology to the wild type Gaussia luciferase, in combination with its function with respect to the duration of light emission as compared to wild type.

Polypeptides

The Gaussia luciferase protein is first expressed with a 17 amino acid leader sequence at it's N-terminus. The amino acid sequence of the wild type Gaussia luciferase polypeptide including the leader sequence is shown in SEQ ID NO: 3. The amino acid sequence of the wild type Gaussia luciferase polypeptide without the leader sequence is shown in SEQ ID NO: 1. The leader sequence is not necessary for expression or function of the wild type or enhanced Gaussia luciferase, and as such, embodiments of the present invention encompass versions that contain the leader sequence, and also version which do not contain the leader sequence.

In one embodiment, the enhanced Gaussia luciferase is a polypeptide with the amino acid sequence set forth in SEQ ID NO: 1, with a substitution mutation at position 43. In one embodiment, the substitution mutation is a conservative substitution mutation (e.g., Leucine, Tyrosine and Isoleucine) to thereby produce either a Leucine, Tyrosine or an Isoleucine at position 43. In one embodiment, the polypeptide has an Isoleucine at position 43. The amino acid sequence of this specific polypeptide is set forth in SEQ ID NO: 2.

In one embodiment, the enhanced Gaussia luciferase polypeptide has the amino acid sequence set forth in SEQ ID NO: 3, with a substitution mutation at position 60. In one embodiment, the substitution mutation is a conservative substitution mutation (e.g., Leucine, Tyrosine and Isoleucine) to thereby produce either a Leucine, Tyrosine or an Isoleucine at position 60. In one embodiment, the polypeptide has an Isoleucine at position 60.

Those of skill in the art will recognize that truncations of the protein, as well as internal deletions, can be made that have little to no effect on the enzymatic activity of a protein. Furthermore, any such reduction in the activity of the enhanced luciferase may still preserve the enhancement of the light emission identified herein, as compared to the same fragment of a non-enhanced wild type luciferase. As such, the present invention is also intended to encompass such functional fragments. Functionality is identified by the same assays described herein for the full length polypeptide, only comparing the fragment to a comparable wild type polypeptide sequence.

Those of skill in the art will recognize that variations on the amino acid sequence of the polypeptide can be made that have little to no effect on the enzymatic activity (e.g., conservative substitution mutations) of the protein. Any such reduction in the activity resulting from a variation on amino acid sequence to the enhanced polypeptide may still preserve the enhancement of the light emission identified herein, as compared to the same variation of a non-enhanced wild type luciferase. As such, the present invention is also intended to encompass such functional variants. Functionality is identified by the assays described herein, comparing the mutated enhanced polypeptide to a comparable mutated (non-enhanced) polypeptide sequence. Such a comparable sequence may, for example, contain a Methionine at the position corresponding to position 43 of SEQ ID NO: 1. In one embodiment, a functional variant has one or more conservative substitution mutations as compared to wild type, in addition to the mutation that produces the enhancement of light emission (e.g., the substitution mutation for Met at the amino acid corresponding to position 43 of SEQ ID NO: 1). Examples of conservative substitutions are provided in the following table:

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |

-continued

| Original residue | Conservative substitution |
| --- | --- |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also possible and may be determined empirically or in accord with known amino acid similarities.

A enhanced Gaussia luciferase polypeptide of the invention, or functional fragment or functional variant thereof, catalyzes a stable light emission output compared to the corresponding "wild type" amino acid sequence, or comparable fragment thereof. In one embodiment, the polypeptide of the present invention, or functional fragment thereof, has an Isoleucine at the position corresponding to position 43 of SEQ ID NO: 1, and the corresponding "wild type" amino acid sequence, has the same length and nucleic acid sequence, but has an M at position 43. Functional variants of the polypeptide of the present invention, can contain additional amino acid substitutions (e.g., conservative) or insertions or deletions, but retain the Isoleucine at the position corresponding to 43 of SEQ ID NO: 1. The corresponding "wild type" amino acid sequence, as the term is used herein, would refer to a comparable polypeptide (identical in length and amino acid sequence), but having an M at the position corresponding to position 43 of SEQ ID NO: 1. Functional variants of functional fragments can also be produced by the skilled artisan, and are encompassed by the present invention.

Comparison of the catalytic activity of the enhanced luciferase polypeptide or functional fragment or variant thereof, of the present invention to wild type polypeptide is to be performed under otherwise identical conditions, appropriate for the bioluminescence reaction. One example of a suitable reaction condition is that of the bacterial lysate assay, described in the Examples section herein. Other reaction conditions are known in the art, and can also be used to identify an enhanced Gaussia luciferase of the present invention. Such reaction conditions can further be used in methods of the present invention, described herein.

Inclusion of a detergent in the reaction conditions will allow the observation of the enhanced light emission duration. In one embodiment, the detergent is Triton X-100, at a concentration of about 0.1% Triton X-100. The enhanced light emission of the luciferase of the present invention may be detected at lower concentrations (e.g., about 0.09, 0.08, 0.07, 0.06, 0.05, 0.04, 0.03, 0.02, or about 0.01% Triton X-100) or at higher concentrations (e.g., about 0.15, 0.16, 0.17, 0.18, 0.19, 0.2, 0.25, 0.3, 0.35, 0.4, 0.45, 0.5, 0.55, 0.6, 0.65, 0.7, 0.75, 0.8, 0.85, 0.9, 0.95, or about 1.0% Triton X-100). The use of alternate detergents may also permit the detection of the enhanced light emission. Other detergents known in the art, include, without limitation, other non-ionic detergents (e.g., Tween-20, Tween-80, Triton X-114, NP40). It may further be possible to detect the enhanced light emission in the presence of an ionic detergent such as ionic detergents like sodium lauryl sulphate or sodium lauryl sarcosyl.

Stable light emission refers to an increase over the comparable "wild type" polypeptide, wherein the increase in light emission is signified by retaining significantly greater percentage of its original light emission in a standard assay, than the comparable "wild type" polypeptide over a set time period. The time period can be at least about 1 minute, about 2 minutes, about 3 minutes, etc. A significantly greater percentage of original light emission is about 30% or greater retention of light emission compared to the wild type polypeptide. In one embodiment, the polypeptide of the invention has about 40% or greater retention of light emission compared to wild type polypeptide over a given assay time period. In one embodiment, the polypeptide of the invention has from about 50%, or more, to about 60%, or more greater retention of light emission compared to wild type polypeptide over a given assay time period. One example of a standard assay is provided in the Examples section described herein. In this assay, the mutant GlucM43I retained over 87% of its original light emission over the first 2 minutes, compared to wild type Gluc which retained only about 30% of its original light emission. This is about a 57% increase in light emission retention.

In one embodiment, the enhanced luciferase polypeptide, functional fragment or functional variant of the present invention is purified to the point where it is substantially pure. In one embodiment, the polypeptide, functional fragment or functional variant of the present invention is contained in an extract (e.g., a cellular extract). In one embodiment, the polypeptide, functional fragment or functional variant of the present invention is contained in a secretion or a fluid of an organism. Such secretions are typically isolated as a biological sample. These and other biological samples are described herein. The present invention further encompasses the polypeptide, functional fragment or functional variant of the present invention contained in a biological sample such as those described herein.

The enhanced luciferase polypeptide of the present invention can be used in any appropriate bioluminescence-generating system. The polypeptide of the present invention can be used in any bioluminescence assay system.

The enhanced luciferase polypeptide of the present invention, functional fragment or functional variant thereof, can further be linked to one or more other molecules (e.g., proteins, nucleic acids, polysaccharides, lipids, etc.) to form a conjugate molecule. As such, another aspect of the present invention relates to the conjugate molecule that comprises the polypeptide of the present invention, functional fragment or functional variant thereof. In one embodiment, the polypeptide, functional fragment or functional variant is linked to at least one other polypeptide. In one embodiment, the other polypeptide(s) is a functional polypeptide sequence (e.g, a marker polypeptide, an affinity tag, an enzyme, a visible or selectable marker, etc.).

Fused Polypeptide Sequences

The enhanced luciferase polypeptide of the present invention may further be linked to other functional polypeptide sequences to thereby produce a conjugate protein. Such linkage may be in the form of an expressed fusion protein. Fusions may be made either at the amino terminus or at the carboxyl terminus of the polypeptide of the present invention, and may be direct with no linker or adapter molecule or may be through a linker or adapter molecule, such as one or more amino acid residues up to about 20 amino acids residues, or up to about 50 amino acid residues. A linker or adapter molecule may also be designed with a cleavage site for a DNA restriction endonuclease or for a protease to allow for separation of the fused moieties. Useful polypeptide sequences for linkage include affinity tags, binding proteins, polypeptides which confer antibiotic resistance, calorimetric markers, polypeptides which have enzymatic function (e.g., beta-lactamase), or are otherwise recognized by an enzyme, and other visible markers. Examples of affinity tags include, without limitation, a biotinylation site, V5 tag, Xpress tag, AU1 tag, T7 tag, VSV-G tag, a DDDDK tag, S tag, CruzTag09, CruzTag 22, CruzTag41, Glu-Glu tag, Ha.11 tag, and a KT3 tag, $(His)_n$, maltose binding protein, thioredoxin, glutathione S-transferase and NusA. Examples of binding proteins include, without limitation include cell-cell and cell-substrate adhesion molecules including ICAMs, integrins, cadherins or selectins, antigenic determinants, and natural ligands.

Nucleic Acids

Aspects of the invention further relate to a nucleic acid having a sequence that encodes the enhanced luciferase polypeptide, functional fragment or functional variant described herein. The nucleic acid can be an isolated fragment, or the fragment can be in the context of a larger nucleic acid sequence (e.g, a vector for expression, additional coding sequences for a fusion protein, etc.) as the result of genetic engineering. Examples of larger nucleic acid sequences useful in the present invention are described herein.

In one embodiment, the nucleic acid fragment comprises the coding sequences of wild type nucleotide sequence of Gaussia luciferase, deposited under GenBank database accession number AY015993, but differs at the codon corresponding to codon 60 (of the luciferase polypeptide including the leader sequence), to thereby encode an amino acid substitution mutation (for Methionine) in the encoded protein. The following table lists codons for the corresponding amino acids.

| | Codons | | |
|---|---|---|---|
| Ala/A | GCT, GCC, GCA, GCG | Leu/L | TTA, TTG, CTT, CTC, CTA, CTG |
| Arg/R | CGT, CGC, CGA, CGG, AGA, AGG | Lys/K | AAA, AAG |
| Asn/N | AAT, AAC | Met/M | ATG |
| Asp/D | GAT, GAC | Phe/F | TTT, TTC |
| Cys/C | TGT, TGC | Pro/P | CCT, CCC, CCA, CCG |
| Gln/Q | CAA, CAG | Ser/S | TCT, TCC, TCA, TCG, AGT, AGC |
| Glu/E | GAA, GAG | Thr/T | ACT, ACC, ACA, ACG |
| Gly/G | GGT, GGC, GGA, GGG | Trp/W | TGG |
| His/H | CAT, CAC | Tyr/Y | TAT, TAC |

-continued

| | Codons | | |
|---|---|---|---|
| Ile/I | ATT, ATC, ATA | Val/V | GTT, GTC, GTA, GTG |
| START | ATG | STOP | TAA, TGA, TAG |

In another embodiment, the nucleic acid fragment comprises the coding sequences of wild type nucleotide sequence of Gaussia luciferase, deposited under GenBank database accession number AY015993, but does not include the codons for the first 17 amino acids (the signal sequence) and differs at the codon corresponding to codon 60 (of the luciferase polypeptide including the leader sequence), to thereby encode an amino acid substitution mutation (for Methionine) in the encoded protein. The wild type nucleic acid coding sequence of Gaussia luciferase is provided in SEQ ID NO: 4. In one embodiment, the nucleic acid fragment of the present invention comprises the nucleic acid sequence set forth in SEQ ID NO: 4, except that the codon corresponding to codon 60 encodes an amino acid substitution mutation (for Methionine) in the encoded protein. In one embodiment, the codon corresponding to codon 60 encodes a conservative substitution mutation (e.g., Isoleucine, Tyrosine, or Leucine). In another embodiment, the nucleic acid fragment of the present invention comprises the nucleic acid sequence corresponding to nt 52-555 of SEQ ID NO: 4, which encodes the luciferase lacking the signal sequence, except that the codon corresponding to codon 60 encodes an amino acid substitution mutation (for Methionine) in the encoded protein. In one embodiment, the codon corresponding to codon 60 encodes a conservative substitution mutation (e.g., Isoleucine, Tyrosine, or Leucine).

In another embodiment, the nucleic acid fragment comprises a nucleotide sequence that has been codon optimized for expression in a certain system (e.g., a mammalian system). In one embodiment, the nucleotide sequence set forth in SEQ ID NO: 5, but differs at the codon corresponding to codon 60, to thereby encode an amino acid substitution mutation in the encoded protein. In one embodiment, the codon corresponding to codon 60 encodes a conservative substitution mutation for Methionine. In one embodiment, the codon encodes either Tyrosine, Leucine or Isoleucine. In one embodiment, the codon encodes Isoleucine. In one embodiment, the nucleic acid fragment does not contain codons corresponding to the signal sequence. In one embodiment, the nucleic acid fragment corresponds to nucleotides 52-555 of SEQ ID NO: 5, but differs at the codon corresponding to codon 60, to thereby encode an amino acid substitution mutation in the encoded protein. In one embodiment, the codon corresponding to codon 60 encodes a conservative substitution mutation for Methionine. In one embodiment, the codon encodes either Tyrosine, Leucine or Isoleucine. In one embodiment, the codon encodes Isoleucine.

Regulatory Sequences

The nucleic acid fragments of the present invention may be operatively linked to additional nucleic acid sequences, e.g., regulatory sequences (also referred to herein as regulatory elements) for expression in a host cell or multicellular organism. The linkage may be in the context of a vector or engineered into genomic DNA. Regulatory sequences that may be useful in nucleic acid constructs, include, but are not limited to, polyadenylation sequences, translation control sequences (e.g., an internal ribosome entry segment, IRES), enhancers, inducible elements, or introns. Such regulatory sequences may not be necessary, although they may increase expression by affecting transcription, stability of the mRNA, translational efficiency, or the like. One or more copies (e.g, concatomeric repeats) of the regulatory sequences may be present. In one embodiment, the regulatory sequence is a promoter. In addition to a promoter, the nucleic acid can be operatively linked to other regulatory sequences. Such regulatory sequences may be linked to the nucleic acid fragments of the present invention as reporter molecules for use in detection of modulation of the regulatory sequences.

Examples of regulatory sequences include, without limitation, p53 response element (TGCCTGGACTTGCCTGG)n (SEQ ID NO: 6); AP-1 (Activator Protein-1 Response element) (TGACTAA)n (SEQ ID NO: 7); C/EBP (ATTGCG-CAAT)n (SEQ ID NO: 8); CRE (cAMP response element) (AGCCTGACGTCAGAG)n (SEQ ID NO: 9); DR1 (DR1 type retinoic acid response element) (AGGTCAN)n (SEQ ID NO: 10); DR3 (DR3 type retinoic acid response element) (AGGTCANNN)n (SEQ ID NO: 11); DR4 (DR4 type retinoic acid response element) (CAGGAGGTCA)n (SEQ ID NO: 12); DR5 (DR5 type retinoic acid response element) (AGGTCANNNNN)n (SEQ ID NO: 13); Egr-1 (early growth response 1) (GGGGTGGGGN)n (SEQ ID NO: 14); GAS (gastrin response element) (AGTTTCATAT-TACTCTAAATC) n (SEQ ID NO: 15); GRE (glucocorticoid response element) (GGTACATTTTGTTCT)n (SEQ ID NO: 16); ISRE (Interferon-stimulated response element) (TAGTTTCACTTTCCC)n (SEQ ID NO: 17); LILRE (IL-1 response element) (TCACTTCCTGAGAG)n (SEQ ID NO: 18); NFAT response element (GGAGGAAAAACT-GTTTCATACAGAAGGCGT)n (SEQ ID NO: 19); NF-κB response element (TGGGGACTTTCCGC)n (SEQ ID NO: 20); SRE (Serum response element) (AGGATGTCCATATT-AGGACATCT)n (SEQ ID NO: 21); SRF (serum response factor or c-fos serum response element) (GTCCATATTAG-GAC)n (SEQ ID NO: 22) TARE (tumor necrosis factor-α response element) (TCTCAATCCACAATCTCGGAGTAT-GTCTAGACTGACAATG)n (SEQ ID NO: 23) or nucleic acids substantially homologous thereto, as that term is defined herein. The term "n" after the sequence bracket refers to the number of tandem repeats, for example the number of tandem repeats can be at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or more than 16, for example, at least 20 or more tandem repeats.

In some embodiments, at the regulatory sequences can be a single regulatory response element or any number of multiple regulatory response elements, or modified regulatory response elements or fragments thereof. Modified regulatory response elements include, for example a change or modification of the nucleic acid sequence of the response element, for example, but not limited to, mutation, methylation, substitution, nucleic acid analogue etc.

In some embodiments, there may be a "spacer" of a limited number of nucleic acids or nucleic acid analogues between each of the regulatory element in a repeat of response element. In some embodiments, such spacers can be at least 1 or at least 2 or at least 3 or at least 4 or a least 5 or at least 6 or at least 7 or more nucleic acids, or nucleic acid analogues between each response element.

Vector Systems

The nucleic acid sequences described herein may be in the context of a nucleic acid backbone typically designed for replication and propagation in a host system (e.g., prokaryotic or viral). Examples of suitable nucleic acid backbones include viral vectors such as retroviral vectors, and also plasmids. In one embodiment, the nucleic acid of the present invention is in the context of a vector or plasmid.

As used herein, vector (or plasmid) refers to discrete elements that are used to introduce heterologous DNA into cells for either expression or replication thereof. The recombinant nucleic acid of such vectors may be circular or linear, double-stranded or single-stranded. The general methods for constructing recombinant nucleic acid which can transform target cells are well known to those skilled in the art, and the same compositions and methods of construction may be utilized to produce the DNA useful herein. For example, Sambrook et al. (1989) provides suitable methods of construction. Selection and use of such vehicles are well within the skill of the artisan. In one embodiment, the vector is an expression vector. An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

Vector can be a plasmid, a reproducible extragenomic vector, etc. The vector may be designed for extragenomic replication in a host cell, or for integration of the nucleic acid sequences into the genome of a recipient host cell.

The vectors of the invention may be introduced to cells by any means including physical/non-biological means (e.g., electroporation) or biological means (e.g., via infection with a viral vector such as a retroviral vector). The vector backbone used should be suitable for the intended host cell. The vector can be readily introduced into the host cell(s), e.g., mammalian, bacterial, yeast or insect cells by any procedure useful for the introduction into a particular cell to yield a transformed containing the nucleic acid sequences (e.g., in extragenomic form as with a plasmid, or stably integrated into its genome). In one embodiment, the nucleic acid sequences are expressed by the host cell. The preferred method(s) of introduction of the vector will depend upon the makeup of the nucleic acid backbone from which it is designed. A variety of vectors designed for the propogation of nucleic acids and also for introduction and incorporation into the genome of a cell are known in the art. Such vectors can be adapted for use as the backbone of the vector of the present invention, for delivery of the nucleic acid sequences of the present invention into a host cell. Such vectors include viral, without limitation, viral based vectors, plasmids, and transposon based vectors such as Sleeping Beauty (U.S. Pat. No. 6,613,752), and also Tol2 transposon based vectors. Such known vectors can be adapted, or a new vectors can be designed, for use as a nucleic acid backbone for the nucleic acid fragments described herein. In one embodiment, the nucleic acid backbone also includes regulatory elements suitable for propagation and selection in E. coli which include an origin of replication (ori) and an antibiotic resistance marker for selection ($Amp^R$). Examples of Tol2 transposon sequences are provided in U.S. Patent Application 2007/0101452.

In one embodiment, the vector is specifically designed for the production of a fusion protein described herein. Such a vector will typically include a polylinker sequence for (in-frame) insertion of a second nucleic acid fragment having an open reading frame, to thereby generate a vector (e.g, an expression vector) for the production of a fusion protein. In one embodiment, the vector contains some restriction endonuclease sites in the polylinker sequence to facilitate subcloning of a peptide-encoding DNA sequence into the vector (e.g., an expression vector), in-frame with the nucleic acid of the present invention, to thereby encode a fusion protein. Typically several such restriction sites are clustered in a single locus in the vector, creating what is commonly called a polylinker. There are often a few charged amino acids encoded by the DNA sequence in such polylinker sequences. Such polylinkers are known in the art, examples of which are provided in U.S. Pat. No. 6,069,230. The polylinker sequence can be located either 5' or 3' to the nucleic acid fragment of the present invention.

Host Cells and Multicellular Organisms

Another aspect of the present invention relates to a host cell or multicellular organism that contains the nucleic acid of the present invention. The term "host" refers to the fact that the nucleic acid is exogenous to the organism, and is introduced by genetic engineering, e.g, by use of a vector system described herein. As such the host is a transgenic organism. In one embodiment, the host expresses the nucleic acid of the present invention. The host cells of the present invention are typically produced by transfection with the vector in the form of a plasmid expression vector, a viral expression vector, or as an isolated linear DNA sequence. The presently described vectors can be introduced to a cell by any of a wide variety of methods known in the art.

Suitable hosts include prokaryotic or eukaryotic organisms, including plant (e.g., *Arabidopsis*, tobacco, etc.), yeast, bacteria, fish (e.g., zebrafish) worm, insect (e.g., *drosophila*) and mammalian. Mammalian cells include, without limitation; primate, human and a cell from any animal of interest, including without limitation; mouse, hamster, rabbit, dog, cat, domestic animals, such as equine, bovine, murine, ovine, canine, feline, etc. The cells may be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoeitic, neural, stromal, muscle, cardiovascular, hepatic, pulmonary, gastrointestinal stem cells, etc. Yeast cells may also be used as cells in this invention.

Methods of Use

Another aspect of the present invention relates to methods of production and use of the polypeptides and nucleic acids described herein. One such method is the generation of the polypeptides, fusion proteins, and reporter constructs described herein. Other methods are to the use of the enhanced luciferase polypeptides, functional fragments or functional variants, described herein, as detectable markers in a variety of systems. Such systems and methods of use include, without limitation, any system in which wild type Gaussia luciferase functions as a suitable marker. Such systems and methods of use, are known in the art. Representative systems and methods of use are disclosed in U.S. Pat. Nos. 6,232,107; 7,709,253; and 6,596,257, and also in applications U.S. Ser. No. 12/355,055, U.S. Ser. No. 12,444,068, PCT/US2009, 055361, the contents of which are incorporated herein by reference.

The presence (e.g., as representing expression) of the enhanced luciferase polypeptide or functional fragment or functional variant of the present invention is assessed by a bioluminescence assay, as a qualitative and/or quantitative measure of the expression and processing of the polypeptide through the secretory pathway in the cells in which it is expressed. In one embodiment, cells grown in culture can be assessed by measurement of the polypeptide secreted into the culture media. In one embodiment, a luciferin, for example but not limited to, coelenterazine and its analogues is added to the culture media, and the bioluminescence monitored. In another embodiment, the media is collected and assayed for bioluminescence. In such an embodiment, the cells can be repeatedly assessed for luciferase activity. Further quantitation of secretion can easily be monitored by taking aliquots of the medium conditioned by living cells over time. Since the cells are not disrupted during assay they can be used for other assays in parallel. Further, since the cells are not disrupted, conditioned media can be sampled repeatedly for time course studies from a single well and cells can be used for further studies, such as RNA or protein analysis.

Since the protein is naturally secreted, the assay is performed on small samples of the conditioned media, with no need to lyse the cells, which makes it much faster and more convenient than assays with other luciferases such as firefly luciferase (FLuc) which is used in the Superlight™ luciferase reporter gene assay (Bioassays, CA) where cell lysis is required. The present invention is advantageous over other systems in that the methods serve to reduce the variability of transfection efficiency when different wells are used. Further, since the Gaussia luciferase is over two thousand fold more sensitive than firefly luciferase (FLuc) or *Renilla* luciferase (Tannous et al., 2005), it can easily be used to measure promoters over a wide range of activities with no need for signal enhancement for promoters with low activity.

One example of such use as a detectable marker in a system is use of the enhanced luciferase polypeptide as a reporter protein in a transcriptional regulatory system. In such a system, the nucleic acid encoding the polypeptide of the present invention is operatively linked to a regulatory element to thereby produce a reporter construct. The reporter construct is used in a compatible system to detect modulation (activation or suppression) of the regulatory element by detection of the expressed polypeptide using a bioluminescence assay system. A compatible system generally involves delivery of the reporter construct (either in vitro or in vivo) to the assay system under conditions suitable for expression from the reporter construct. Such systems include in vivo (e.g, multicellular organisms) and in vitro (e.g., cell culture) assay systems. Modulation of polypeptide expression reflects modulation of the activity of the regulatory element. Modulation of the polypeptide expression is detected by monitoring the amount of expressed polypeptide, and is determined in a bioluminescence assay system. Modulation can be in response to an environmental stimulus of the cell or organism, or in response to an added effector, or a test agent suspected as having modulatory activity, etc. In one embodiment, modulation and detection is in a high-throughput assay system.

In another embodiment, the enhanced luciferase polypeptide or functional fragment or functional variant thereof, can be used to study signaling pathways in cells. In such an embodiment, the regulatory sequences operatively linked to the polypeptide are responsive to particular signaling molecules. As an exemplary example, the regulatory sequence can be responsive to a protein kinase signaling molecule, as a non-limiting example, PKC, and the regulatory sequence is operatively linked to nucleic acid encoding the polypeptide of the present invention. The activation of the signaling molecule will activate or inhibit the regulatory sequence and can be detected by bioluminescence. The activity of the signaling molecule can be assessed in response to environmental stimuli by assessing changes in bioluminescence in the media and/or fluorescence in the cell. For example, activation of NFκB transcription factor and early growth factors responsive (Egr-1) factor, as well as p53 apoptosis induction in response to environmental stimuli.

In another embodiment, the enhanced luciferase polypeptide or functional fragment or variant thereof, can be used to monitor cell viability and cell death. In this invention, the secretion of the luciferase is proportion to the cell number, therefore the level of bioluminescence can be used as a method to measure the number of cells. Accordingly, in such an embodiment, the nucleic acid the present invention is operative linked to a regulatory sequence encoding a constitutively active promoter. In one embodiment of the invention relates to methods monitor the viability of cells by bioluminescence in response to environmental stimuli. In one embodiment, the environmental stimuli can be intrinsic environmental stimuli. Accordingly, the methods of this invention can be used to monitor cell death over time in the same well by repeated assay of the conditioned media for Gluc activity, since as cells die, the synthesis and secretion of the luciferase is attenuated. In such an embodiment, a decrease in the bioluminescence signal compared to control cells indicates an increase in cell death as the cells are dye and there are less cells present, whereas an increase in bioluminescence indicates cell viability and in some instances a possible increase in cell proliferation. In one embodiment, the method is performed on proliferating cells. In another embodiment, the method is performed on non-dividing cells, for example terminally differentiated cells or cell that have undergone mitotic arrest, for example with treatment with mitomycin-c or other mitotic altering agents known to persons skilled in the art. The cells do not need to be disrupted by the sampling procedure, so the Gaussia luciferase viability assay has an advantage over the firefly luciferase (FLuc) cell viability assay (Bioassays) in that no cell-lysis is required. The viability assay also has an advantage over other apoptosis detection assays, such as CellQuanti-MTT™ cell Viability assay kits (Bioassays) as in those cases the reagents need to be added to the cells, which makes it impossible to do time course measurements in the same well.

The enhanced luciferase polypeptide, functional fragment or functional variant thereof, can further be used as a marker in other systems (e.g., biological). In one embodiment, the enhanced luciferase polypeptide, functional fragment or functional variant thereof is linked to another molecule (e.g., protein), and used to detect the presence of the molecule. Linkage can be by any means to produce a conjugate molecule. In one embodiment, linkage is by co-expression as a fusion protein. Such a conjugate molecule can be used in an assay system, e.g., a high-throughput assay system, to detect the presence of the attached molecule in a bioluminescence assay.

The enhanced luciferase polypeptide, fragment or variant thereof used in such systems can be detected as a secretion, and as such the luciferase protein that is secreted over time can be monitored. Another alternative is to compare the amount of luciferase protein produced from differently treated samples to one another, and to different control samples.

Aspects of the present invention further relate to an assay system comprising the enhanced luciferase polypeptide of the present invention, or functional fragment or functional variant thereof. In such an assay system, the luciferase activity of the polypeptide of the present invention is used to detect the presence of the polypeptide, wherein the presence of the polypeptide, is an indicator of an event having taken place in a host cell or system. Such an even can be, for example, activation of a regulatory element. Examples of such assay systems are known in the art, with a few such examples described herein. The assay system may further comprise a host cell comprising the nucleic acid fragment encoding the polypeptide, as described herein, in expressible form. In one embodiment, the assay system is a high-throughput assay system.

Kits

Kits comprising one or more components (e.g., assay system components) described herein are also encompassed by the present invention. Such kits will typically contain printed instructions as to the use of the components contained therein.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention is further illustrated by the following Examples. These Examples are provided to aid in the understanding of the invention and are not construed as a limitation thereof.

The present invention can be defined in any of the following numbered paragraphs:

1. An isolated nucleic acid fragment comprising a sequence of nucleotides encoding a polypeptide comprising the amino acid sequence set forth in SEQ ID NO: 1, with a substitution mutation at the position 43, or a functional fragment thereof, wherein the polypeptide catalyzes a stable light emission output in the presence of a detergent, as compared to a comparable polypeptide which has a Methionine at position 43.
2. The isolated nucleic acid fragment of paragraph 1, wherein the detergent is Triton X-100, present in the amount of 0.1%.
3. The isolated nucleic acid fragment of paragraph 1, wherein the substitution mutation is a conservative mutation
4. The isolated nucleic acid fragment of paragraph 3, wherein the conservative substitution mutation is the substitution of Tyrosine, Leucine and Isoleucine.
5. The isolated nucleic acid fragment of paragraph 4, wherein the substitution mutation is an Isoleucine for Methionine.
6. The isolated nucleic acid fragment of paragraph 1, wherein the nucleotide sequence corresponds to nucleotides 52-555 of SEQ ID NO: 4, with a nucleotide change in codon 60 that results in an amino acid substitution mutation.
7. The isolated nucleic acid fragment of paragraph 1, wherein the nucleotide sequence corresponds to nucleotides 52-555 of SEQ ID NO: 5, with a nucleotide change in codon 60 that results in an amino acid substitution mutation.
8. The isolated nucleic acid fragment of paragraphs 6 or 7, wherein the substitution mutation is a conservative substitution mutation for Methionine.
9. The isolated nucleic acid fragment of paragraph 8, wherein the conservative substitution mutation is a substitution of Tyrosine, Leucine or Isoleucine.
10. The isolated nucleic acid fragment of paragraph 8, wherein the conservative substitution mutation is a substitution of Isoleucine.
11. The isolated nucleic acid fragment of paragraphs 1-10, which further comprises and is operatively linked to a nucleic acid fragment encoding an additional functional polypeptide sequence.
12. The isolated nucleic acid fragment of paragraph 11, wherein the additional functional polypeptide sequence is selected from the group consisting of an affinity tag, an enzyme, and a visible marker.
13. The isolated nucleic acid fragment of paragraphs 1-12, which further comprises and is operatively linked to a regulatory response element.
14. A plasmid comprising the nucleic acid fragment of paragraphs 1-13.
15. An expression vector comprising the nucleic acid fragment of paragraphs 1-13.
16. The expression vector of paragraph 15, further comprising a polylinker region for in-frame sub-cloning of a nucleic acid encoding a second polypeptide sequence.
17. A cell comprising the nucleic acid fragment of paragraphs 1-13.
18. A cell comprising the expression vector of paragraphs 15 or 16.
19. A transgenic organism comprising the nucleic acid fragment of paragraphs 1-13.
20. A polypeptide comprising the amino acid sequence set forth in SEQ ID NO: 1, with a substitution mutation at the position 43, or a functional fragment thereof, wherein the polypeptide catalyzes a stable light emission output in the presence of a detergent, as compared to a comparable polypeptide which has a methionine at position 43.

21. The polypeptide or functional fragment thereof of paragraph 20, wherein the substitution mutation is a conservative mutation.
22. The polypeptide or functional fragment thereof of paragraph 20, wherein the conservative substitution mutation is the substitution of Tyrosine, Leucine and Isoleucine.
23. The polypeptide or functional fragment thereof of paragraph 20, wherein the substitution mutation is an Isoleucine for Methionine.
24. The polypeptide or functional fragment thereof of paragraphs 20-23, which further comprises an additional functional polypeptide sequence.
25. The polypeptide or functional fragment thereof of paragraph 24, wherein the additional functional polypeptide sequence is selected from the group consisting of an affinity tag, an enzyme, and a visible marker.
26. The polypeptide or functional fragment thereof of paragraphs 20-25, wherein the polypeptide or functional fragment is substantially pure.
27. The polypeptide of paragraphs 20-26 wherein the detergent is Triton X-100.
28. An assay system comprising a polypeptide comprising the amino acid sequence set forth in SEQ ID NO: 1, with a substitution mutation at the position 43, or a functional variant or functional fragment thereof, wherein the polypeptide catalyzes a stable light emission output in the presence of a detergent, as compared to a comparable polypeptide which has a Methionine at position 43.
29. An assay system comprising a nucleic acid fragment of any of paragraphs 1-13.
30. An assay system comprising a host cell comprising a nucleic acid fragment of any of paragraphs 1-13.
31. The assay system of paragraphs 28 or 29 that is a high-throughput assay.
32. A method of detecting modulation of a regulatory element, comprising:
    a) providing a nucleic acid encoding the polypeptide or functional fragment thereof, of claim 20, operatively linked to the regulatory element under conditions suitable for expression; and
    b) detecting modulation of the expression of the polypeptide in a bioluminescence assay system wherein the detected modulation indicates like modulation of the regulatory element.
33. A method of detecting a molecule in a biological assay, comprising:
    a) providing the molecule in the form of a linkage to the polypeptide or functional fragment thereof, of paragraph 20; and
    b) detecting the presence of the polypeptide with a bioluminescence assay, to thereby detect the presence of the molecule.
34. A polypeptide comprising the amino acid sequence set forth in SEQ ID NO: 1, with a substitution mutation at the position 43, or a functional variant or functional fragment thereof, wherein the polypeptide catalyzes a stable light emission output in the presence of a detergent, as compared to a comparable polypeptide which has a Methionine at position 43.
35. A method of detecting modulation of a regulatory element, comprising:
    a) providing a nucleic acid encoding the polypeptide or functional variant or fragment thereof, of paragraph 34, operatively linked to the regulatory element under conditions suitable for expression; and
    b) detecting modulation of the expression of the polypeptide in a bioluminescence assay system wherein the detected modulation indicates like modulation of the regulatory element.
36. A method of detecting a molecule in a biological assay, comprising:
    a) providing the molecule in the form of a linkage to the polypeptide or functional variant or fragment thereof, of paragraph 34; and
    b) detecting the presence of the polypeptide with a bioluminescence assay, to thereby detect the presence of the molecule.
37. A kit comprising the expression vector of paragraphs 15 or 16, and instructions.

EXAMPLES

A novel pool of Gaussia luciferase variants created using error-prone PCR and directed molecular evolution techniques was screened for the ability to potentiate stable light output after addition of coelenterazine substrate.[17] Bacteria were transformed with the library and colonies were misted with coelenterazine solution (Gluc substrate) and imaged using a CCD camera at different time points. Colonies which retained high signal over a five-minute period were picked and small scale bacterial cultures for each of the promising clones were grown. Crude cell lysates were then prepared and a kinetic assay was performed upon coelenterazine addition. Initially, 10 different clones were observed to retain stable luminescence activity as compared to the control. Upon confirmation analysis, one clone retained higher luminescence over 10 minutes compared to the other clones and wild-type (wt) Gluc (data not shown). DNA sequencing of this mutant Gluc clone revealed a single nucleotide change which resulted in a change of methionine 43 to isoleucine (FIG. 3). This variant was named GlucM43I.

Figure 4:
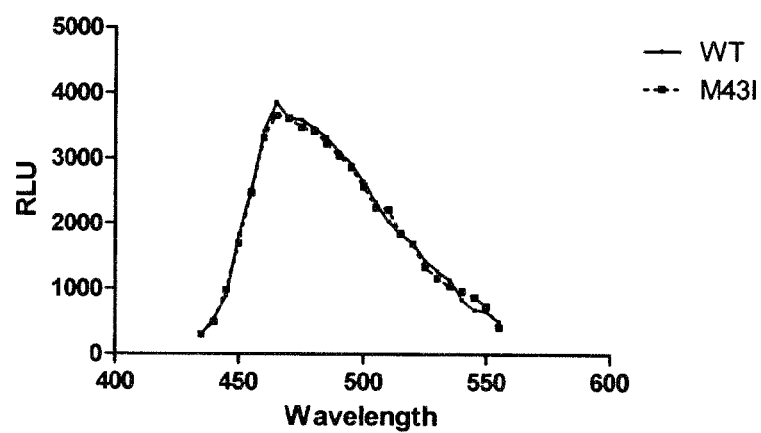
FIG. 4 is a graphical representation of spectral analysis of wt Gluc and GlucM43I. Small scale cultures of bacterial transformed with plasmids encoding wt Gluc and GlucM43I were lysed, mixed with coelenterazine, and a spectral emission analysis was performed.

A comparison of the wt Gluc with GlucM43I activity was performed in bacterial lysates. Cells were lysed using 30 mM Tris-HCl pH 8.0, 2 mM EDTA, 0.1% Triton X-100. A five-minute bioluminescence kinetic assay revealed a clear difference in light emission between the wt and the mutant enzyme (FIG. 1A). Over the first 2 minutes, wt Gluc retained only 30% of its starting activity while the mutant GlucM43I retained over 87% of its original light emission. Spectral analysis of GlucM43I yielded a similar peak in signal when compared to wt Gluc with no shifts in emission spectra (FIG. 4).

Next, the wt and GlucM43I (without the native signal sequence) were cloned into a pET-based expression plasmid in which both cDNAs were cloned in frame between an N-terminal pelB periplasmic signal sequence and a C-terminal 6-His tag. Upon expression, the pelB signal sequence is cleaved and therefore it is not part of the protein. (Since it was isolated from cytoplasm maybe some still has signal sequence and that is why it runs at 25 kd.) Both wt Gluc as well as GlucM43I were purified from bacterial extracts using a 6-His fusion tag and visualized on a coomassie stained gel (not shown).

Figure 5:
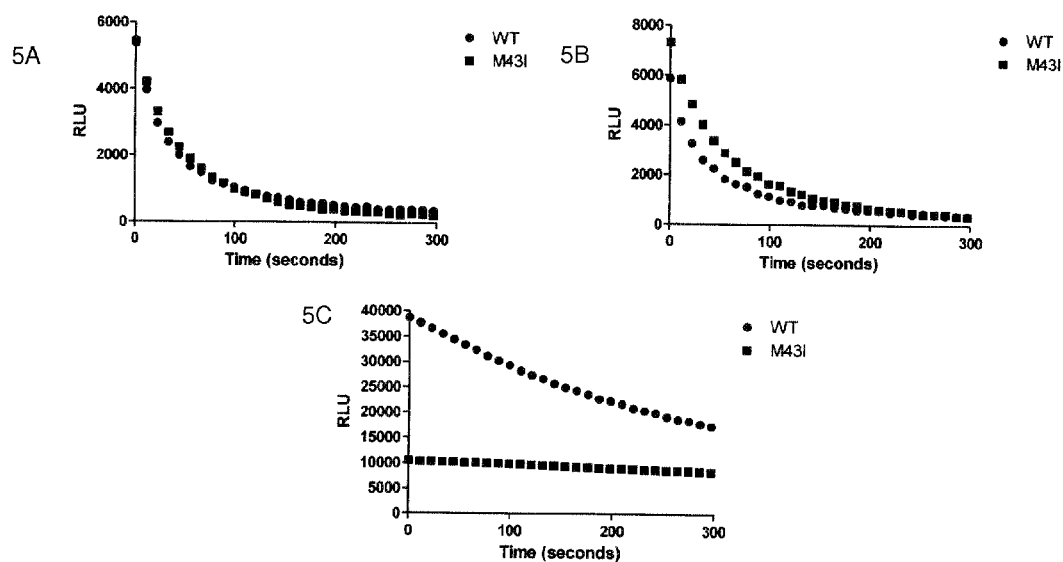
FIG. 5A-FIG. 5C is three graphs showing data from kinetic analysis of purified GlucM43I. A) 10 ng of luciferase was diluted in 30 mM Tris, pH 8.0, and mixed with an equal volume of 20 µM coelenterazine diluted in the same buffer. B) the same conditions as A) except luciferase and coelenterazine were diluted in PBS pH 7.6. C) the same conditions as A) except 0.1% Triton-X-100 was included in the luciferase dilution buffer.

The purified Gluc enzymes (10 ng each) were diluted in 30 mM Tris, pH 8.0, mixed with coelenterazine, and subjected to a 5-minute kinetic analysis. Surprisingly, virtually no difference in the light decay kinetics was observed between wt Gluc and GlucM43I (FIG. 5A). Similar results were observed when enzyme was diluted into phosphate buffered saline pH 7.6 (FIG. 5B). Since detergent was used in the experiments with crude bacterial extracts (FIG. 1A), the presence of the detergent Triton X-100 was checked to see if it had an effect on the Gluc kinetics. A kinetic analysis (as in FIG. 5A) was performed in the presence of 0.1% Triton X-100 in the enzyme dilution buffer (30 mM Tris, pH 8.0). Interestingly, the addition of the detergent Triton X-100 changed the light emission kinetics of reactions catalyzed by both wt Gluc and GlucM43I as quantified using the luminometer and visualized using the CCD camera (FIG. 1B and data not shown; FIG. 5C). Over the five minute assay, there was a decline in activity of 56.6% and 21.3% for wt Gluc and GlucM43I, respectively. Also, the addition of detergent enhanced the initial signal of wt Gluc by 7.1-fold and GlucM43I by 1.9-fold (FIG. 5). A 20 minute kinetic assay using 10 ng of luciferase showed a 3.1-fold increase in the half-life of light emission catalyzed by GlucM43I (930 sec) compared to wt Gluc (330 sec) (data not shown). These results suggest that the detergent Triton X-100 plays a key role in stabilizing the GlucM43I light emission. Thus, all subsequent experiments (unless stated otherwise) were carried out by in the presence of 0.1% Triton X-100.

No significant difference was found between the specific activity of wt Gluc and GlucM43I in the absence of Triton X-100, however in the presence of this detergent, a statistically significant increase (3.7-fold, $P<0.05$) was observed in the specific activity of wt Gluc compared to GlucM43I (FIG. 1C). Furthermore, the addition of Triton X-100 significantly ($P<0.05$) enhanced the specific activity of both wt Gluc (6.3-fold) and GlucM43I (1.88-fold) compared to the respective enzyme in the absence of detergent (FIG. 1C).

To determine the effect of substrate concentration on light emission kinetics, 10 ng of either wt Gluc or GlucM43I was mixed with different concentrations of coelenterazine (diluted in 30 mM Tris-HCl pH 8.0, 0.1% Triton X-100) and a five-minute kinetic assay was analyzed. For wt Gluc, higher light decay occurred with higher substrate concentrations (FIG. 6A). On the other hand, the light emission kinetics catalyzed by the GlucM43I variant were not affected (FIG. 6B). Light decay kinetics (5 minute assay) for both wt Gluc and GlucM43I were relatively unaffected over an 8-fold range of enzyme concentration (FIGS. 7A &B).

The data described above used Gluc purified from bacteria. To demonstrate the expanded applicability of the GlucM43I variant, its ability to catalyze enhanced light stability in the presence of Triton X-100 when expressed in and secreted from mammalian cells was analyzed. 293T human kidney fibroblast cells were transiently transfected with a mammalian expression vector encoding either wt Gluc or GlucM43I. Forty-eight hours later, 5 µl aliquots of conditioned medium were transferred to a 96 well plate and subsequently 95 µl of coelenterazine diluted in 30 mM Tris, 5 mM NaCl, pH 8.0 containing 0.1% Triton X-100 was added to each well. Kinetic analysis revealed that GlucM43I catalyzed approximately 7-fold more stable light emission as compared to wt Gluc (FIG. 1D). Bioluminescence reaction catalyzed by GlucM43I retained 81% of original light emission compared to 12.6% for wt Gluc over a 10 minute period ($P<0.0001$).

Figure 2:
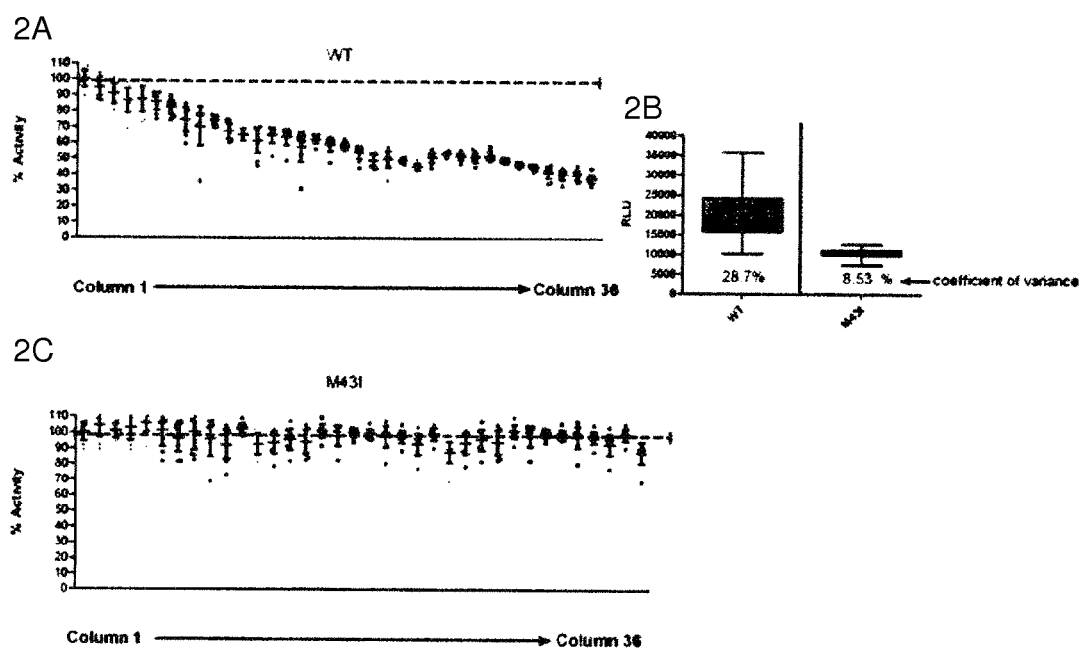
FIG. 2A-FIG. 2C shows three graphs which indicate that GlucM43I will serve as a tool for high-throughput applications. Ten ng of either wt Gluc or GlucM43I variant in 30 mM Tris, pH 8.0, 0.1% Triton X-100 was pipetted into three 96 well plates. An equal volume of 20 µM coelenterazine in PBS with was then rapidly added to all wells using a multi-channel pipette and each plate was then sequentially read in a microplate luminometer. (A, B) Scatter plot of signals obtained from either wt Gluc (A) or GlucM43I (B) presented in a column by column basis. In both cases, the plates were read from left to right. Data presented as % Gluc activity in which the first well read is set to 100%. Error bars represent standard deviation. (C) Box plot representation of the spread of total well readings for both wt Gluc and GlucM43I. All data are representative of three independent experiments.
Figure 8:
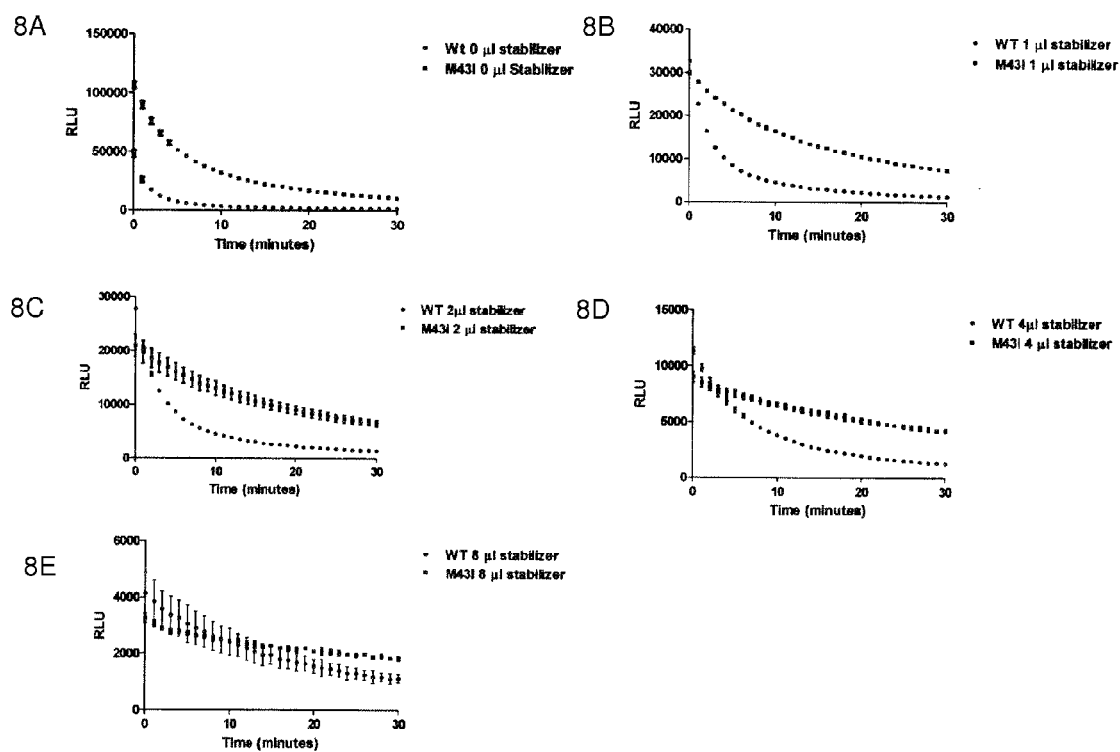
FIG. 8A-FIG. 8E is a collection of 5 graphs showing data from kinetics of light decay of wt Gluc and GlucM43I using a commercially available light stabilizing kit. Luciferases were missed in assay buffer containing coelenterazine with the indicated amount of stabilizer (A-E) and a 30 minute kinetic assay was performed.

As Gluc displays flash-type light emission kinetics, it is necessary to use a luminometer with a built-in injector to assay its activity. Generally, when using an injector, more substrate is used (to purge the instrument before each assay) and higher reading time/well is required (generally 10 sec reading and integrating signal over 2 sec). This high reading time limits the use of Gluc for high-throughput screening applications. To determine whether the stability of light emission catalyzed by GlucM43I in the presence of Triton X-100 would make the Gluc assay suited for high-throughput screening, a 1-second read/well of 288 wells (three 96 well plates) was performed, each containing 10 ng of wt or GlucM43I. Coelenterazine was dilute in 30 mM Tris-HCl pH 8.0, 0.1% Triton X-100 and added to all wells simultaneously using a multi-channel pipette. The data was analyzed based on the way the luminometer reads the wells (column by column on the plate) and presented in column format where signals from the left represent the earliest reads and those on the right represent later reads. For wt Gluc, a >62% decrease in RLU between the first and last well was observed (FIG. 2A). For GlucM43I, the RLU was much more consistent between first and last well (~12% decrease; FIG. 2B). The coefficient of variation was calculated to be 28.7% for wt Gluc and only 8.53% for GlucM43I (FIG. 2C). Furthermore, an F test for unequal variance revealed a significant difference between the two groups ($P<0.0001$).

wt Gluc was next compared with GlucM43I using the only available buffer system for stabilizing light emission catalyzed by Gluc (New England Biolabs; LumiFlex™ Gluc Assay Kit). This kit consists of a proprietary assay buffer and "stabilizer" solution, which are mixed together with coelenterazine solution and Gluc. The drawback of using this system is that the stabilizer dramatically affects the Gluc sensitivity by up to one order of magnitude (manufacturer's data). The effect of this assay system on the stability and light output of wt Gluc versus GlucM43I was tested by mixing 40 ng of either enzyme with coelenterazine diluted in the assay buffer containing different amounts (1-8 µl) of stabilizer. The light-emission kinetics was monitored over a 30 minute period. The results are presented in Table I and FIG. 8.

TABLE I

| | Condition | | | |
|---|---|---|---|---|
| | WT GLUC | | GlucM43I | |
| 40 ng Gluc | Average Starting RLU | Average Half life (min) | Average Starting RLU | Average Half life (min) |
| Lumiflex buffer No stabilizer | $4.82 \times 10^4$ ($+/-3.1 \times 10^3$) | 1.05 ($+/-0.07$) | $1.1 \times 10^5$ ($+/-2.9 \times 10^3$) | 4.45* ($+/-0.07$) |
| Lumiflex buffer 1 µl stabilizer | $3.27 \times 10^4$ ($+/-6.3 \times 10^1$) | 2.05 ($+/-0.07$) | $2.99 \times 10^4$ ($+/-4.0 \times 10^2$) | 11.9* ($+/-0.14$) |
| Lumiflex buffer 2 ul stabilizer | $2.78 \times 10^4$ ($+/-8.9 \times 10^1$) | 2.55 ($+/-0.06$) | $2.09 \times 10^4$ ($+/-2.1 \times 10^3$) | 15.6* ($+/-0.14$) |
| Lumiflex buffer 4 ul stabilizer | $1.1 \times 10^4$ ($+/-3.2 \times 10^2$) | 5.45 ($+/-0.07$) | $8.99 \times 10^3$ ($+/-4.9 \times 10^2$) | 26.05* ($+/-0.78$) |
| Lumiflex buffer 8 ul stabilizer | $4.1 \times 10^3$ ($+/-7.3 \times 10^2$) | 12.95 ($+/-0.21$) | $3.25 \times 10^3$ ($+/-1.6 \times 10^2$) | 32.8*# ($+/-1.13$) |

TABLE I-continued

| | Condition | | | |
|---|---|---|---|---|
| | WT GLUC | | GlucM43I | |
| 40 ng Gluc | Average Starting RLU | Average Half life (min) | Average Starting RLU | Average Half life (min) |
| 30 mM Tris pH 8.0, 0.1% Triton X-100 | $1.90 \times 10^5$ (+/−$2.3 \times 10^3$) | 2.35 (+/−0.07) | $4.76 \times 10^4$ (+/−$3.4 \times 10^3$) | 9.1*[#] (+/−0.28) |

Light emission kinetics using commercially available Gluc kit
*denotes statistically significant difference from wt Gluc under identical conditions ($P < 0.05$)
[#]denotes value extrapolated from kinetic assay using linear regression GlucM43I outperformed wt Gluc under all conditions with a 2.3 to 6.1-fold increase in the half-life of light emission. Importantly, under conditions of nearly equivalent light stability, the initial starting RLU value was 7 to 10-fold higher for the GlucM43I variant as compared to the wild type (wt Gluc with 8 µl stabilizer compared to GlucM43I with 1 µl stabilizer or wt Gluc with 4 µl stabilizer compared to GlucM43I with no stabilizer). The half-life of light emission of GlucM43I under the highest amount of stabilizer (8 µl) was 32.8 minutes compared to 12.95 minutes for wt Gluc. A good combination of stability and signal output was obtained for GlucM43I as compared to the wild type under our assay conditions using 40 ng of either enzyme with 30 mM Tris pH 8.0, 0.1% Triton X-100 (Table I).

In summary, a variant (GlucM43I) of Gaussia luciferase was isolated from a screen of a mutant library created by DNA shuffling and error-prone PCR that catalyzes a stable light emission output as compared to the wild type Gluc in the presence of a detergent, Triton X-100. This Gluc variant proved to be very useful for high-throughput screening applications where sensitivity and stable light emission are desired. Since Gaussia luciferase is naturally secreted, it allows functional screening and kinetic analysis from a single well by measuring an aliquot of conditioned medium at different time points, leaving the cells intact for conformational analysis. Gluc is the only reporter available for high-throughput applications which allows kinetics analysis. Further, Gluc has the advantage over other fluorescent and bioluminescent reporters in that its level in the blood correlates to the level of its activity in a given biological system, thereby allowing semi-throughput screening/validation of novel therapeutics in vivo.

Methods

Construction of Gluc Library.

A library comprised of a pool of mutant Gluc enzymes was created by shuffling of DNA fragments generated using error-prone PCR. First, the full human codon-optimized DNA sequence encoding for Gaussia luciferase[14] was PCR-amplified using Taq polymerase (5 PRIME, Fisher Scientific, Pittsburgh, Pa.) and flanking primers which included EcoRI (upstream primer) and XhoI (downstream primer) restriction sites using the following conditions in a Applied Biosystems 2720 thermalcycler: 1 cycle of 94° C.-2 min.; 35 cycles of 94° C.-30 sec., 58° C.-30 sec, 72° C. 30 sec; 1 cycle of 72° C. for 7 min. The PCR product was digested using 0.3 Units of DNaseI (NCew England Biolabs, Ipswich, Mass.) for 10 min at room temperature and inactivated with addition of EDTA and 75° C. for 15 min. The digested DNA was separated on a 2% agarose gel and fragments from ~50-150 base pairs were carefully excised using a sterile scalpel and the gel slice was placed in 3,500 MWCO dialysis tubing (Fisher Scientific, Pittsburgh, Pa.) and the DNA was eluted into TBE by electrophoresing for 15 min at 120V. The DNA was then ethanol precipitated, resuspended in nuclease-free water and the PCR fragments were reassembled into the full-sized product using a PCR with Extensor Hi-Fidelity PCR enzyme mix (Thermo Scientific, Portsmouth, N.H.) and no primers using the following thermalcycler conditions: 1 cycle, 94° C.-2 min.; 40 cycles, 94°-30 sec, 45° C.-30 sec, 68° C.-30 sec. One microliter from this reaction served as template for a second PCR using the flanking primers used above following the following conditions: 1 cycle, 94° C.-2 min; 25 cycles, 94° C.-30 sec, 58° C.-30 sec, 68° C.-30 sec; 1 cycle, 68° C.-7 min. The PCR product was gel extracted, digested with EcoRI and XhoI and ligated with a similarly digested pHGCx expression vector.[14]

Screening Procedure.

The vector containing the mutant Gluc sequences created above was transformed into DH10B bacteria and plated on 5-15 cm LB-Ampicillin Agar plates. Approximately 2000 well isolated colonies (representing individual Gluc clones) were obtained on all the plates. To ensure that the DNA shuffling procedure had been successful, plasmid DNA from 10 clones was isolated and subjected to DNA sequencing. On average clones displayed 1-2 changes in the corresponding amino acid sequence when compared to the native enzyme. To measure light output kinetics of all of the colonies, a 20 µM solution of coelenterazine in 1×PBS was misted onto the surface of the plate (one plate analyzed at a time). Light emission was immediately measured using a cryogenically cooled, high efficiency CCD camera system (Roper Scientific). The level of luciferase activity was measured by recording total photon counts in the CCD camera (10 sec exposure) with no illumination. The plate was imaged again 5 min post-spray. An image of the plate to allow orientation of colony location with light emission was taken at the end of the imaging session using illumination of the box.

Determining clones with promising light stability was accomplished by comparing the mean value of light emission of each clone at t=0 with that of the same clone at t=5 min. Ten clones which displayed the greatest degree of stability in light emission were picked with a sterile pipette tip and 5 ml LB cultures were grown overnight. Each culture was pelleted and the bacteria resuspended in 300 µl of a lysis buffer consisting of 30 mM Tris-HCl pH 8.0, 2 mM EDTA, 0.1% Triton X-100. After three freeze/thaw cycles the cell debris were pelleted with a 5 min spin at 13,000 rpm in a microcentrifuge. Forty microliters of the clarified lysate was mixed with an equal volume of 20 µM coelenterazine in 1×PBS in a 96 medium binding flat well plate (Greiner bio-one, Monroe, N.C.). A 5 min kinetic assay was performed using 11 sec read intervals in a Molecular Devices Spectra Max Gemini XS luminometer connected to a computer using SOFTmax Pro software. The Gluc encoding region from the most promising clone (M43I)

was then subjected to DNA sequencing. Both wt Gluc and GlucM43I were cloned in-frame with a 6-histidine tag sequence in pET26b(+) vector (Novagen, Gibbstown, N.J.; Supplementary Methods).

Enzyme Purification.

The DNA encoding for the native Gluc as well as M43I were PCR-amplified using specific primers and cloned in-frame with the 6-histidine tag sequence in pET26b(+) vector (Novagen, Gibbstown, N.J.) using BamHI and XhoI sites. Gene expression is under the control of an isopropyl β-D-1-thiogalactopyranoside (IPTG)-inducible T7 RNA polymerase promoter. The Gluc signal sequence was not included in the construct utilized for the data in this study. Similar to what had been reported, this was found to severely affect protein yield in bacteria (Inouye, S.; Sahara, Y. Biochem Biophys Res Commun 2008, 365, 96-101.).[1] The pET vectors encoding the 6His-tagged native Gluc and GlucM43I variant were transformed into competent HMS174 bacteria. Overnight cultures were diluted 1:40 into 200 ml of fresh LB containing 30 μg/ml kanamycin and grown to an $OD_{600}$ of 0.6 at room temperature. At this time, protein expression was induced with 20 μM IPTG and cultures were grown for 18 h at room temperature. Cells were pelleted by centrifuging for 15 min at 10,000×g and resuspended in 10 ml Bugbuster Master Mix (Novagen, Gibbstown, N.J.) containing Benzonase. Insoluble debris was pelleted via another spin. The clarified lysate was filtered through a 45 μm syringe filter and loaded onto a nickel charged resin column (Novagen) equilibrated with binding buffer (0.5 M NaCl, 20 mM Tris-HCl, 5 mM imidazole, pH 7.9). The column was rinsed with 20 volumes of binding buffer and next with 18 volumes of wash buffer (0.5 M NaCl, 20 mM Tris-HCl, 60 mM imidazole, pH 7.9). His-tagged Gluc and GlucM43I were eluted from the column with 1.2 ml of elution buffer (0.5 M NaCl, 20 mM Tris-HCl, 1 M imidazole, pH 7.9) collecting 200 μl fractions. The fractions containing the highest Gluc activity were pooled and dialyzed against 30 mM Tris-HCl, pH 8.0 overnight using 3500 MWCO dialysis tubing (Fisher Scientific, Portsmouth, N.H.). Glycerol was added to a final concentration of 10%. Protein concentration was determined by Bradford assay (BioRad, Hercules, Calif.) and purity determined by SDS-PAGE analysis using a NuPAGE□ 10% Bis-Tris gel (Invitrogen) and coomassie blue staining. The faint band observed at ~20 kDa for both constructs likely represents the absence of the pelB signal peptide (2.1 kDa) which is included in the pET26b (+) vector to allow for periplasmic fractions.

Determination of Enzymatic Activity.

The specific activity for the purified Gluc enzymes was determined by performing a flash bioluminescence assay on 10 ng of protein in 50 μl of 30 mM Tris-HCl pH 8.0 in wells of a 96 well plate. To this 50 μl of 20 μM coelenterazine in PBS/5 mM NaCl was injected and bioluminescent signal measured in a microtiter plate luminometer (Dynex Technologies, Chantilly, Va.). From these readings the RLU/mg protein was calculated. To determine effects of buffer pH and composition, 10 ng of purified native Gluc or GlucM43I variant were diluted in 30 mM Tris-HCl, pH 8.0 with or without 0.1% Triton X-100 (Fisher Biotech) or in 1× phosphate buffered saline pH 7.6 (Invitrogen). For analysis of different substrate concentrations on light emission kinetics, 10 ng of enzyme was diluted in 50 μl of 30 mM Tris-HCl, 0.1% Triton X-100, pH 8.0 and then mixed with an equal volume of the specified concentration of coelenterazine in PBS/5 mM NaCl. For analysis of different enzyme concentration on light emission kinetics the specified amount of enzyme was diluted in 50 μl 30 mM Tris-HCl, 0.1% Triton X-100, pH 8.0 and then mixed with an equal volume of 20 μM coelenterazine in PBS/5 mM NaCl. Reaction kinetics of both wt and mutant Gluc was also visualized using a cooled CCD camera by putting 10 ng of each Gluc in a 96-well plate in triplicates followed by the addition of 50 μl coelenterazine (20 μM) diluted in 30 mM Tris-HCl, 0.1% Triton X-100, pH 8.0. The plate was imaged using the CCD camera at different time points by acquiring photon counts over 1 sec.

Multiplate Stability Assay.

10 ng of purified Gluc (native or GlucM43I) in 50 μl of 30 mM Tris-HCl, 0.1% Triton X-100, pH 8.0 was pipetted into each of 3-96 well plates. Next 50 μl 20 μM coeletenrazine in PBS/5 mM NaCl was rapidly pipetted into each well using a 12 well multichannel pipette. The plates were then read in the order of substrate addition using a 1 second read time in the microplate reader luminometer.

Stability of Light Emission Catalyzed by Gluc Enzymes from Media Harvested from Transfected Mammalian Cells.

293T human fibroblast cells (provided by Dr. Michele Calos, Stanford Univ. Sch. Med.) were seeded in 6 well plates at a density of $4 \times 10^5$ cells/well. The following day the cells were transfected with the mammalian expression vector encoding Gluc or GlucM43I (both with secretion signal sequence) under the control of CMV promoter using Lipofectamine (Invitrogen). Forty-eight hours post-transfection, conditioned medium was harvested, cell debris pelleted by a 1 min high-speed spin in a microcentrifuge and the media was transferred to a fresh microcentrifuge tube. For light emission kinetic analysis of Gluc in media, 5 μl of media was pipetted into wells of a 96 well plate. Immediately following addition of 95 μl 40 μM of coelenterazine in a solution of 30 mM Tris, 0.1% Triton X-100, 5 mM NaCl, pH 8.0, a 10 minute kinetic analysis was performed using a luminometer.

NEB Lumiflex™ Gluc Assay.

The assay was performed according to manufacturer's instructions. Briefly, 25 μl of either wt Gluc or GlucM43I variant diluted in 30 mM Tris pH 8.0 was mixed with 1× assay buffer containing 1× coelenterazine solution and the indicated amount of stabilizer. Immediately after mixing, a 30-minute kinetic assay was performed as before using the Molecular Devices Spectra Max Gemini XS luminometer.

Statistical Analysis.

Data presented provides the mean value±the standard deviation. In some figures, group comparisons were computed by an unpaired Student's t-test using GraphPad PRISM software (version 5.0, San Diego, Calif.).

REFERENCES (1) Massoud, T. F.; Gambhir, S. S. *Genes Dev* 2003, 17, 545-580.
(2) de Wet, J. R.; Wood, K. V.; Helinski, D. R.; DeLuca, M. *Proc Natl Acad Sci USA* 1985, 82, 7870-7873.
(3) Contag, C. H.; Ross, B. D. *J Magn Reson Imaging* 2002, 16, 378-387.
(4) Bhaumik, S.; Gambhir, S. S. *Proc Natl Acad Sci USA* 2002, 99, 377-382.
(5) Greer, L. F., 3rd; Szalay, A. A. *Luminescence* 2002, 17, 43-74.
(6) Badr, C. E.; Hewett, J. W.; Breakefield, X. O.; Tannous, B. A. *PLoS ONE* 2007, 2, e571.
(7) Ketteler, R.; Sun, Z.; Kovacs, K. F.; He, W. W.; Seed, B. *Genome Biol* 2008, 9, R64.
(8) Lee, J. Y.; Kim, S.; Hwang do, W.; Jeong, J. M.; Chung, J. K.; Lee, M. C.; Lee, D. S. *J Nucl Med* 2008, 49, 285-294.
(9) Remy, I.; Michnick, S. W. *Nat Methods* 2006, 3, 977-979.

(10) Santos, E. B.; Yeh, R.; Lee, J.; Nikhamin, Y.; Punzalan, B.; Punzalan, B.; La Perle, K.; Larson, S. M.; Sadelain, M.; Brentjens, R. J. *Nat Med* 2009, 15, 338-344.
(11) Suzuki, T.; Usuda, S.; Ichinose, H.; Inouye, S. *FEBS Lett* 2007, 581, 4551-4556.
(12) Verhaegent, M.; Christopoulos, T. K. *Anal Chem* 2002, 74, 4378-4385.
(13) Wurdinger, T.; Badr, C.; Pike, L.; de Kleine, R.; Weissleder, R.; Breakefield, X. O.; Tannous, B. A. *Nat Methods* 2008, 5, 171-173.
(14) Tannous, B. A.; Kim, D. E.; Fernandez, J. L.; Weissleder, R.; Breakefield, X. O. *Mol Ther* 2005, 11, 435-443.
(15) Hewett, J. W.; Tannous, B.; Niland, B. P.; Nery, F. C.; Zeng, J.; Li, Y.; Breakefield, X. O. *Proc Natl Acad Sci USA* 2007, 104, 7271-7276.
(16) Wiles, S.; Ferguson, K.; Stefanidou, M.; Young, D. B.; Robertson, B. D. *Appl Environ Microbiol* 2005, 71, 3427-3432.
(17) Stemmer, W. P. *Nature* 1994, 370, 389-391.

The invention claimed is:

1. An isolated nucleic acid fragment comprising a nucleotide sequence encoding a polypeptide comprising the amino acid sequence set forth in SEQ ID NO: 1, with a substitution mutation at the position 43, or a functional fragment thereof, wherein the polypeptide catalyzes a stable light emission output in the presence of a detergent, as compared to a comparable polypeptide which has a Methionine at position 43.

2. The isolated nucleic acid fragment of claim 1, wherein the detergent is Triton X-100, present in the amount of 0.1%.

3. The isolated nucleic acid fragment of claim 1, wherein the substitution mutation is a conservative mutation 4. The isolated nucleic acid fragment of claim 3, wherein the conservative substitution mutation is the substitution of Tyrosine, Leucine and Isoleucine.

5. The isolated nucleic acid fragment of claim 4, wherein the substitution mutation is an Isoleucine for Methionine.

6. The isolated nucleic acid fragment of claim 1, wherein the nucleotide sequence corresponds to nucleotides 52-555 of SEQ ID NO: 4, or to nucleotides 52-555 of SEQ ID NO: 5, with a nucleotide change in codon 60 that results in an amino acid substitution mutation.

7. The isolated nucleic acid fragment of claim 6, wherein the substitution mutation is a conservative substitution mutation for Methionine.

8. The isolated nucleic acid fragment of claim 7, wherein the conservative substitution mutation is a substitution of Tyrosine, Leucine or Isoleucine.

9. The isolated nucleic acid fragment of claim 7, wherein the conservative substitution mutation is a substitution of Isoleucine.

10. The isolated nucleic acid fragment of claim 1, which further comprises and is operatively linked to a nucleic acid fragment encoding an additional functional polypeptide sequence.

11. The isolated nucleic acid fragment of claim 10, wherein the additional functional polypeptide sequence is selected from the group consisting of an affinity tag, an enzyme, and a visible marker.

12. The isolated nucleic acid fragment of claim 1, which further comprises and is operatively linked to a regulatory response element.

13. A cell comprising an expression vector comprising the nucleic acid fragment of claim 1.

14. A polypeptide comprising the amino acid sequence set forth in SEQ ID NO: 1, with a substitution mutation at the position 43, or a functional fragment thereof, wherein the polypeptide catalyzes a stable light emission output in the presence of a detergent, as compared to a comparable polypeptide which has a methionine at position 43.

15. The polypeptide or functional fragment thereof of claim 14, wherein the substitution mutation is a conservative mutation.

16. The polypeptide or functional fragment thereof of claim 14, wherein the conservative substitution mutation is the substitution of Tyrosine, Leucine and Isoleucine.

17. The polypeptide or functional fragment thereof of claim 14, wherein the substitution mutation is an Isoleucine for Methionine.

18. The polypeptide or functional fragment thereof of claim 14, which further comprises an additional functional polypeptide sequence.

19. The polypeptide or functional fragment thereof of claim 18, wherein the additional functional polypeptide sequence is selected from the group consisting of an affinity tag, an enzyme, and a visible marker.

20. The polypeptide or functional fragment thereof of claim 14, wherein the polypeptide or functional fragment is substantially pure.

* * * * *

SEQUENCE LISTING

```
<160> NUMBER OF SEQ ID NOS: 26

<210> SEQ ID NO 1
<211> LENGTH: 168
<212> TYPE: PRT
<213> ORGANISM: Gaussia princeps

<400> SEQUENCE: 1

Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
            20                  25                  30

Lys Lys Leu Pro Leu Glu Val Leu Lys Glu Met Glu Ala Asn Ala Arg
        35                  40                  45

Lys Ala Gly Cys Thr Arg Gly Cys Leu Ile Cys Leu Ser His Ile Lys
    50                  55                  60

Cys Thr Pro Lys Met Lys Lys Phe Ile Pro Gly Arg Cys His Thr Tyr
65                  70                  75                  80

Glu Gly Asp Lys Glu Ser Ala Gln Gly Gly Ile Gly Glu Ala Ile Val
                85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
        115                 120                 125

Lys Gly Leu Ala Asn Val Gln Cys Ser Asp Leu Leu Lys Lys Trp Leu
    130                 135                 140

Pro Gln Arg Cys Ala Thr Phe Ala Ser Lys Ile Gln Gly Gln Val Asp
145                 150                 155                 160

Lys Ile Lys Gly Ala Gly Gly Asp
                165

<210> SEQ ID NO 2
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
            20                  25                  30

Lys Lys Leu Pro Leu Glu Val Leu Lys Glu Ile Glu Ala Asn Ala Arg
        35                  40                  45

Lys Ala Gly Cys Thr Arg Gly Cys Leu Ile Cys Leu Ser His Ile Lys
    50                  55                  60
```

```
Cys Thr Pro Lys Met Lys Lys Phe Ile Pro Gly Arg Cys His Thr Tyr
 65                  70                  75                  80

Glu Gly Asp Lys Glu Ser Ala Gln Gly Gly Ile Gly Glu Ala Ile Val
                 85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
        115                 120                 125

Lys Gly Leu Ala Asn Val Gln Cys Ser Asp Leu Leu Lys Lys Trp Leu
    130                 135                 140

Pro Gln Arg Cys Ala Thr Phe Ala Ser Lys Ile Gln Gly Gln Val Asp
145                 150                 155                 160

Lys Ile Lys Gly Ala Gly Gly Asp
                165

<210> SEQ ID NO 3
<211> LENGTH: 184
<212> TYPE: PRT
<213> ORGANISM: Gaussia princeps

<400> SEQUENCE: 3

Met Gly Val Lys Val Leu Phe Ala Leu Ile Cys Ile Ala Val Ala Glu
  1               5                  10                  15

Ala Lys Pro Thr Glu Asn Asn Glu Asp Phe Asn Ile Val Ala Val Ala
                 20                  25                  30

Ser Asn Phe Ala Thr Thr Asp Leu Asp Ala Asp Arg Gly Lys Leu Pro
             35                  40                  45

Gly Lys Lys Leu Pro Leu Glu Val Leu Lys Glu Met Ala Asn Ala Arg
 50                  55                  60

Lys Ala Gly Cys Thr Arg Gly Cys Leu Ile Cys Leu Ser His Ile Lys
 65                  70                  75                  80

Cys Thr Pro Lys Met Lys Lys Phe Ile Pro Gly Arg Cys His Thr Tyr
                 85                  90                  95

Glu Gly Asp Lys Glu Ser Ala Gln Gly Gly Ile Gly Glu Ala Ile Val
            100                 105                 110

Asp Ile Pro Glu Ile Pro Gly Phe Lys Asp Leu Glu Pro Met Glu Gln
        115                 120                 125

Phe Ile Ala Gln Val Asp Leu Cys Val Asp Cys Thr Thr Gly Cys Leu
    130                 135                 140

Lys Gly Leu Ala Asn Val Gln Cys Ser Asp Leu Leu Lys Lys Trp Leu
145                 150                 155                 160

Pro Gln Arg Cys Ala Thr Phe Ala Ser Lys Ile Gln Gly Gln Val Asp
                165                 170                 175

Lys Ile Lys Gly Ala Gly Gly Asp
            180

<210> SEQ ID NO 4
<211> LENGTH: 555
<212> TYPE: DNA
<213> ORGANISM: Gaussia princeps

<400> SEQUENCE: 4
atgggagtga aagttctttt tgcccttatt tgtattgctg tggccgaggc caaaccaact      60
gaaaacaatg aagatttcaa cattgtagct gtagctagca actttgctac aacggatctc     120
gatgctgacc gtggtaaatt gcccggaaaa aaattaccac ttgaggtact caaagaaatg     180
```

```
gaagccaatg ctaggaaagc tggctgcact aggggatgtc tgatatgcct gtcacacatc      240
aagtgtacac ccaaaatgaa gaagtttatc ccaggaagat gccacaccta tgaaggagac      300
aaagaaagtg cacagggagg aataggagag gctattgttg acattcctga aattcctggg      360
tttaaggatt tggaacccat ggaacaattc attgcacaag ttgacctatg tgtagactgc      420
acaactggat gcctcaaagg tcttgccaat gtgcaatgtt ctgatttact caagaaatgg      480
ctgccacaaa gatgtgcaac ttttgctagc aaaattcaag gccaagtgga caaaataaag      540
ggtgccggtg gtgat                                                       555

<210> SEQ ID NO 5
<211> LENGTH: 558
<212> TYPE: DNA
<213> ORGANISM: Gaussia princeps

<400> SEQUENCE: 5
atgggagtca aagttctgtt tgccctgatc tgcatcgctg tggccgaggc caagcccacc       60
gagaacaacg aagacttcaa catcgtggcc gtggccagca acttcgcgac cacggatctc      120
gatgctgacc gcgggaagtt gcccggcaag aagctgccgc tggaggtgct caaagagatg      180
gaagccaatg cccggaaagc tggctgcacc aggggctgtc tgatctgcct gtcccacatc      240
aagtgcacgc ccaagatgaa gaagttcatc ccaggacgct gccacaccta cgaaggcgac      300
aaagagtccg cacagggcgg cataggcgag gcgatcgtcg acattcctga gattcctggg      360
ttcaaggact tggagcccat ggagcagttc atcgcacagg tcgatctgtg tgtggactgc      420
acaactggct gcctcaaagg gcttgccaac gtgcagtgtt ctgacctgct caagaagtgg      480
ctgccgcaac gctgtgcgac ctttgccagc aagatccagg ccaggtgga caagatcaag      540 ggggccggtg gtgactag                                                    558

<210> SEQ ID NO 6
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(340)
<223> OTHER INFORMATION: This sequence may encompass 2-16 or 20
      "TGCCTGGACTTGCCTGG" repeating units
<220> FEATURE:
<223> OTHER INFORMATION: See specification as filed for detailed
      description of substitutions and preferred embodiments

<400> SEQUENCE: 6
tgcctggact tgcctggtgc ctggacttgc ctggtgcctg gacttgcctg gtgcctggac       60
ttgcctggtg cctggacttg cctggtgcct ggacttgcct ggtgcctgga cttgcctggt      120
gcctggactt gcctggtgcc tggacttgcc tggtgcctgg acttgcctgg tgcctggact      180
tgcctggtgc ctggacttgc ctggtgcctg gacttgcctg gtgcctggac ttgcctggtg      240
cctggacttg cctggtgcct ggacttgcct ggtgcctgga cttgcctggt gcctggactt      300
gcctggtgcc tggacttgcc tggtgcctgg acttgcctgg                            340

<210> SEQ ID NO 7
<211> LENGTH: 140
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(140)
<223> OTHER INFORMATION: This sequence may encompass 2-16 or 20
      "TGACTAA" repeating units
<220> FEATURE:
<223> OTHER INFORMATION: See specification as filed for detailed
      description of substitutions and preferred embodiments

<400> SEQUENCE: 7
tgactaatga ctaatgacta atgactaatg actaatgact aatgactaat gactaatgac    60
taatgactaa tgactaatga ctaatgacta atgactaatg actaatgact aatgactaat   120
gactaatgac taatgactaa                                                140

<210> SEQ ID NO 8
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 2-16 or 20
      "ATTGCGCAAT" repeating units
<220> FEATURE:
<223> OTHER INFORMATION: See specification as filed for detailed
      description of substitutions and preferred embodiments

<400> SEQUENCE: 8
attgcgcaat attgcgcaat attgcgcaat attgcgcaat attgcgcaat attgcgcaat    60
attgcgcaat attgcgcaat attgcgcaat attgcgcaat attgcgcaat attgcgcaat   120
attgcgcaat attgcgcaat attgcgcaat attgcgcaat attgcgcaat attgcgcaat   180
attgcgcaat attgcgcaat                                                200

<210> SEQ ID NO 9
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 2-16 or 20
      "AGCCTGACGTCAGAG" repeating units
<220> FEATURE:
<223> OTHER INFORMATION: See specification as filed for detailed
      description of substitutions and preferred embodiments

<400> SEQUENCE: 9
agcctgacgt cagagagcct gacgtcagag agcctgacgt cagagagcct gacgtcagag    60
agcctgacgt cagagagcct gacgtcagag agcctgacgt cagagagcct gacgtcagag   120
agcctgacgt cagagagcct gacgtcagag agcctgacgt cagagagcct gacgtcagag   180
agcctgacgt cagagagcct gacgtcagag agcctgacgt cagagagcct gacgtcagag   240
agcctgacgt cagagagcct gacgtcagag agcctgacgt cagagagcct gacgtcagag   300
```

```
<210> SEQ ID NO 10
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(140)
<223> OTHER INFORMATION: This sequence may encompass 2-16 or 20
      "AGGTCAN" repeating units
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (56)..(56)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: modified_base
<222> LOCATION: (98)..(98)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other
```

-continued

```
<220> FEATURE:
<221> NAME/KEY: modified_base
<222> LOCATION: (119)..(119)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (133)..(133)
<223> OTHER INFORMATION: a, c, t, g, unknown or other
<220> FEATURE:
<221> NAME/KEY: modified_base
<222> LOCATION: (140)..(140)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 10
aggtcanagg tcanaggtca naggtcanag gtcanaggtc anaggtcana ggtcanaggt     60
canaggtcan aggtcanagg tcanaggtca naggtcanag gtcanaggtc anaggtcana   120
ggtcanaggt canaggtcan                                               140

<210> SEQ ID NO 11
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(180)
<223> OTHER INFORMATION: This sequence may encompass 2-16 or 20
      "AGGTCANNN" repeating units
<220> FEATURE:
<221> NAME/KEY: modified_base
<222> LOCATION: (7)..(9)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: modified_base
<222> LOCATION: (25)..(27)
<223> OTHER INFORMATION: a, c, t, g, unknown or other
<220> FEATURE:
<221> NAME/KEY: modified_base
<222> LOCATION: (34)..(36)
<223> OTHER INFORMATION: a, c, t, g, unknown or other
<220> FEATURE:
<221> NAME/KEY: modified_base
<222> LOCATION: (43)..(45)
<223> OTHER INFORMATION: a, c, t, g, unknown or other
<220> FEATURE:
<221> NAME/KEY: modified_base
<222> LOCATION: (52)..(54)
<223> OTHER INFORMATION: a, c, t, g, unknown or other
<220> FEATURE:
<221> NAME/KEY: modified_base
<222> LOCATION: (61)..(63)
<223> OTHER INFORMATION: a, c, t, g, unknown or other
<220> FEATURE:
<221> NAME/KEY: modified_base
<222> LOCATION: (70)..(72)
<223> OTHER INFORMATION: a, c, t, g, unknown or other
<220> FEATURE:
<221> NAME/KEY: modified_base
<222> LOCATION: (79)..(81)
<223> OTHER INFORMATION: a, c, t, g, unknown or other
```

<220> FEATURE:
<221> NAME/KEY: modified_base
<222> LOCATION: (88)..(90)
<223> OTHER INFORMATION: a, c, t, g, unknown or other
<220> FEATURE:
<221> NAME/KEY: modified_base
<222> LOCATION: (97)..(99)
<223> OTHER INFORMATION: a, c, t, g, unknown or other
<220> FEATURE:
<221> NAME/KEY: modified_base
<222> LOCATION: (106)..(108)
<223> OTHER INFORMATION: a, c, t, g, unknown or other
<220> FEATURE:
<221> NAME/KEY: modified_base
<222> LOCATION: (115)..(117)
<223> OTHER INFORMATION: a, c, t, g, unknown or other
<220> FEATURE:
<221> NAME/KEY: modified_base
<222> LOCATION: (124)..(126)
<223> OTHER INFORMATION: a, c, t, g, unknown or other
<220> FEATURE:
<221> NAME/KEY: modified_base
<222> LOCATION: (133)..(135)
<223> OTHER INFORMATION: a, c, t, g, unknown or other
<220> FEATURE:
<221> NAME/KEY: modified_base
<222> LOCATION: (142)..(144)
<223> OTHER INFORMATION: a, c, t, g, unknown or other
<220> FEATURE:
<221> NAME/KEY: modified_base
<222> LOCATION: (151)..(153)
<223> OTHER INFORMATION: a, c, t, g, unknown or other
<220> FEATURE:
<221> NAME/KEY: modified_base
<222> LOCATION: (160)..(162)
<223> OTHER INFORMATION: a, c, t, g, unknown or other
<220> FEATURE:
<221> NAME/KEY: modified_base
<222> LOCATION: (169)..(171)
<223> OTHER INFORMATION: a, c, t, g, unknown or other
<220> FEATURE:
<221> NAME/KEY: modified_base
<222> LOCATION: (178)..(180)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 11
aggtcannna ggtcannnag gtcannnagg tcannnaggt cannnaggtc annnaggtca    60
nnnaggtcan nnaggtcann naggtcannn aggtcannna ggtcannnag gtcannnagg   120
tcannnaggt cannnaggtc annnaggtca nnnaggtcan nnaggtcann naggtcannn   180

<210> SEQ ID NO 12
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 2-16 or 20
      "CAGGAGGTCA" repeating units
<220> FEATURE:
<223> OTHER INFORMATION: See specification as filed for detailed
      description of substitutions and preferred embodiments

<400> SEQUENCE: 12
caggaggtca caggaggtca caggaggtca caggaggtca caggaggtca caggaggtca    60
caggaggtca caggaggtca caggaggtca caggaggtca caggaggtca caggaggtca   120

```
caggaggtca caggaggtca caggaggtca caggaggtca caggaggtca caggaggtca    180
caggaggtca caggaggtca                                                 200
```

<210> SEQ ID NO 13
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(220)
<223> OTHER INFORMATION: This sequence may encompass 2-16 or 20
      "AGGTCANNNNN" repeating units
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (18)..(22)
<223> OTHER INFORMATION: a, c, t, g, unknown or other
<220> FEATURE:
<221> NAME/KEY: modified_base
<222> LOCATION: (29)..(33)
<223> OTHER INFORMATION: a, c, t, g, unknown or other
<220> FEATURE:
<221> NAME/KEY: modified_base
<222> LOCATION: (40)..(44)
<223> OTHER INFORMATION: a, c, t, g, unknown or other
<220> FEATURE:
<221> NAME/KEY: modified_base
<222> LOCATION: (51)..(55)
<223> OTHER INFORMATION: a, c, t, g, unknown or other
<220> FEATURE:
<221> NAME/KEY: modified_base
<222> LOCATION: (62)..(66)
<223> OTHER INFORMATION: a, c, t, g, unknown or other
<220> FEATURE:
<221> NAME/KEY: modified_base
<222> LOCATION: (73)..(77)
<223> OTHER INFORMATION: a, c, t, g, unknown or other
<220> FEATURE:
<221> NAME/KEY: modified_base
<222> LOCATION: (84)..(88)
<223> OTHER INFORMATION: a, c, t, g, unknown or other
<220> FEATURE:
<221> NAME/KEY: modified_base
<222> LOCATION: (95)..(99)
<223> OTHER INFORMATION: a, c, t, g, unknown or other
<220> FEATURE:
<221> NAME/KEY: modified_base
<222> LOCATION: (106)..(110)
<223> OTHER INFORMATION: a, c, t, g, unknown or other
<220> FEATURE:
<221> NAME/KEY: modified_base
<222> LOCATION: (117)..(121)
<223> OTHER INFORMATION: a, c, t, g, unknown or other
<220> FEATURE:
<221> NAME/KEY: modified_base
<222> LOCATION: (128)..(132)
<223> OTHER INFORMATION: a, c, t, g, unknown or other
<220> FEATURE:
<221> NAME/KEY: modified_base
<222> LOCATION: (139)..(143)
<223> OTHER INFORMATION: a, c, t, g, unknown or other
<220> FEATURE:
<221> NAME/KEY: modified_base
<222> LOCATION: (150)..(154)
<223> OTHER INFORMATION: a, c, t, g, unknown or other
<220> FEATURE:
<221> NAME/KEY: modified_base
<222> LOCATION: (161)..(165)
<223> OTHER INFORMATION: a, c, t, g, unknown or other

```
<220> FEATURE:
<221> NAME/KEY: modified_base
<222> LOCATION: (172)..(176)
<223> OTHER INFORMATION: a, c, t, g, unknown or other
<220> FEATURE:
<221> NAME/KEY: modified_base
<222> LOCATION: (183)..(187)
<223> OTHER INFORMATION: a, c, t, g, unknown or other
<220> FEATURE:
<221> NAME/KEY: modified_base
<222> LOCATION: (194)..(198)
<223> OTHER INFORMATION: a, c, t, g, unknown or other
<220> FEATURE:
<221> NAME/KEY: modified_base
<222> LOCATION: (205)..(209)
<223> OTHER INFORMATION: a, c, t, g, unknown or other
<220> FEATURE:
<221> NAME/KEY: modified_base
<222> LOCATION: (216)..(220)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 13
aggtcannnn naggtcannn nnaggtcann nnnaggtcan nnnnaggtca nnnnnaggtc      60
annnnnaggt cannnnnagg tcannnnnag gtcannnnna ggtcannnnn aggtcannnn     120
naggtcannn nnaggtcann nnnaggtcan nnnnaggtca nnnnnaggtc annnnnaggt     180
cannnnnagg tcannnnnag gtcannnnna ggtcannnnn                          220

<210> SEQ ID NO 14
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 2-16 or 20
      "GGGGTGGGGN" repeating units
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base
<222> LOCATION: (60)..(60)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
```

```
<220> FEATURE:
<221> NAME/KEY: modified_base
<222> LOCATION: (90)..(90)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (110)..(110)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other
<220> FEATURE:
<221> NAME/KEY: modified_base
<222> LOCATION: (130)..(130)
<223> OTHER INFORMATION: a, c, t, g, unknown or other
<220> FEATURE:
<221> NAME/KEY: modified_base
<222> LOCATION: (140)..(140)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (160)..(160)
<223> OTHER INFORMATION: a, c, t, g, unknown or other
<220> FEATURE:
<221> NAME/KEY: modified_base
<222> LOCATION: (170)..(170)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (190)..(190)
<223> OTHER INFORMATION: a, c, t, g, unknown or other
<220> FEATURE:
<221> NAME/KEY: modified_base
<222> LOCATION: (200)..(200)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 14
ggggtggggn ggggtggggn ggggtggggn ggggtggggn ggggtggggn ggggtggggn      60
ggggtggggn ggggtggggn ggggtggggn ggggtggggn ggggtggggn ggggtggggn     120
ggggtggggn ggggtggggn ggggtggggn ggggtggggn ggggtggggn ggggtggggn     180
ggggtggggn ggggtggggn                                                 200

<210> SEQ ID NO 15
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(420)
<223> OTHER INFORMATION: This sequence may encompass 2-16 or 20
      "AGTTTCATATTACTCTAA-ATC" repeating units
<220> FEATURE:
<223> OTHER INFORMATION: See specification as filed for detailed
      description of substitutions and preferred embodiments
```

<400> SEQUENCE: 15

```
agtttcatat tactctaaat cagtttcata ttactctaaa tcagtttcat attactctaa    60
atcagtttca tattactcta aatcagtttc atattactct aaatcagttt catattactc   120
taaatcagtt tcatattact ctaaatcagt ttcatattac tctaaatcag tttcatatta   180
ctctaaatca gtttcatatt actctaaatc agtttcatat tactctaaat cagtttcata   240
ttactctaaa tcagtttcat attactctaa atcagtttca tattactcta atcagtttc    300 atattactct aaatcagttt catattactc taaatcagtt tcatattact ctaaatcagt   360
ttcatattac tctaaatcag tttcatatta ctctaaatca gtttcatatt actctaaatc   420
```

<210> SEQ ID NO 16
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 2-16 or 20
      "GGTACATTTTGTTCT" repeating units
<220> FEATURE:
<223> OTHER INFORMATION: See specification as filed for detailed
      description of substitutions and preferred embodiments

<400> SEQUENCE: 16

```
ggtacatttt gttctggtac attttgttct ggtacatttt gttctggtac attttgttct    60
ggtacatttt gttctggtac attttgttct ggtacatttt gttctggtac attttgttct   120
ggtacatttt gttctggtac attttgttct ggtacatttt gttctggtac attttgttct   180
ggtacatttt gttctggtac attttgttct ggtacatttt gttctggtac attttgttct   240
ggtacatttt gttctggtac attttgttct ggtacatttt gttctggtac attttgttct   300
```

<210> SEQ ID NO 17
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 2-16 or 20
      "TAGTTTCACTTTCCC" repeating units
<220> FEATURE:
<223> OTHER INFORMATION: See specification as filed for detailed
      description of substitutions and preferred embodiments

<400> SEQUENCE: 17

```
tagtttcact ttccctagtt tcactttccc tagtttcact ttccctagtt tcactttccc    60
tagtttcact ttccctagtt tcactttccc tagtttcact ttccctagtt tcactttccc   120
tagtttcact ttccctagtt tcactttccc tagtttcact ttccctagtt tcactttccc   180
tagtttcact ttccctagtt tcactttccc tagtttcact ttccctagtt tcactttccc   240
tagtttcact ttccctagtt tcactttccc tagtttcact ttccctagtt tcactttccc   300
```

<210> SEQ ID NO 18
<211> LENGTH: 280
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(280)
<223> OTHER INFORMATION: This sequence may encompass 2-16 or 20
      "TCACTTCCTGAGAG" repeating units
<220> FEATURE:
<223> OTHER INFORMATION: See specification as filed for detailed
      description of substitutions and preferred embodiments

<400> SEQUENCE: 18
tcacttcctg agagtcactt cctgagagtc acttcctgag agtcacttcc tgagagtcac      60
ttcctgagag tcacttcctg agagtcactt cctgagagtc acttcctgag agtcacttcc     120
tgagagtcac ttcctgagag tcacttcctg agagtcactt cctgagagtc acttcctgag     180
agtcacttcc tgagagtcac ttcctgagag tcacttcctg agagtcactt cctgagagtc     240
acttcctgag agtcacttcc tgagagtcac ttcctgagag                           280

<210> SEQ ID NO 19
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(600)
<223> OTHER INFORMATION: This sequence may encompass 2-16 or 20
      "GGAGGAAAAACTGTTT-CATACAGAAGGCGT" repeating units
<220> FEATURE:
<223> OTHER INFORMATION: See specification as filed for detailed
      description of substitutions and preferred embodiments

<400> SEQUENCE: 19
ggaggaaaaa ctgtttcata cagaaggcgt ggaggaaaaa ctgtttcata cagaaggcgt      60
ggaggaaaaa ctgtttcata cagaaggcgt ggaggaaaaa ctgtttcata cagaaggcgt     120
ggaggaaaaa ctgtttcata cagaaggcgt ggaggaaaaa ctgtttcata cagaaggcgt     180
ggaggaaaaa ctgtttcata cagaaggcgt ggaggaaaaa ctgtttcata cagaaggcgt     240
ggaggaaaaa ctgtttcata cagaaggcgt ggaggaaaaa ctgtttcata cagaaggcgt     300
ggaggaaaaa ctgtttcata cagaaggcgt ggaggaaaaa ctgtttcata cagaaggcgt     360
ggaggaaaaa ctgtttcata cagaaggcgt ggaggaaaaa ctgtttcata cagaaggcgt     420
ggaggaaaaa ctgtttcata cagaaggcgt ggaggaaaaa ctgtttcata cagaaggcgt     480
ggaggaaaaa ctgtttcata cagaaggcgt ggaggaaaaa ctgtttcata cagaaggcgt     540
ggaggaaaaa ctgtttcata cagaaggcgt ggaggaaaaa ctgtttcata cagaaggcgt     600

<210> SEQ ID NO 20
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(280)
<223> OTHER INFORMATION: This sequence may encompass 2-16 or 20
      "TGGGGACTTTCCGC" repeating units
<220> FEATURE:
<223> OTHER INFORMATION: See specification as filed for detailed
      description of substitutions and preferred embodiments
```

<400> SEQUENCE: 20

```
tggggacttt ccgctgggga ctttccgctg gggactttcc gctggggact ttccgctggg      60
gactttccgc tggggacttt ccgctgggga ctttccgctg gggactttcc gctggggact     120
ttccgctggg gactttccgc tggggacttt ccgctgggga ctttccgctg gggactttcc     180
gctggggact ttccgctggg gactttccgc tggggacttt ccgctgggga ctttccgctg     240
gggactttcc gctggggact ttccgctggg gactttccgc                           280
```

<210> SEQ ID NO 21
<211> LENGTH: 460
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(460)
<223> OTHER INFORMATION: This sequence may encompass 2-16 or 20 "AGGATGTCCATATTAGGA-CATCT" repeating units
<220> FEATURE:
<223> OTHER INFORMATION: See specification as filed for detailed description of substitutions and preferred embodiments

<400> SEQUENCE: 21

```
aggatgtcca tattaggaca tctaggatgt ccatattagg acatctagga tgtccatatt      60
aggacatcta ggatgtccat attaggacat ctaggatgtc catattagga catctaggat     120
gtccatatta ggacatctag gatgtccata ttaggacatc taggatgtcc atattaggac     180
atctaggatg tccatattag gacatctagg atgtccatat taggacatct aggatgtcca     240
tattaggaca tctaggatgt ccatattagg acatctagga tgtccatatt aggacatcta     300
ggatgtccat attaggacat ctaggatgtc catattagga catctaggat gtccatatta     360
ggacatctag gatgtccata ttaggacatc taggatgtcc atattaggac atctaggatg     420
tccatattag gacatctagg atgtccatat taggacatct                           460
```

<210> SEQ ID NO 22
<211> LENGTH: 280
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(280)
<223> OTHER INFORMATION: This sequence may encompass 2-16 or 20 "GTCCATATTAGGAC" repeating units
<220> FEATURE:
<223> OTHER INFORMATION: See specification as filed for detailed description of substitutions and preferred embodiments

<400> SEQUENCE: 22

```
gtccatatta ggacgtccat attaggacgt ccatattagg acgtccatat taggacgtcc      60
atattaggac gtccatatta ggacgtccat attaggacgt ccatattagg acgtccatat     120
taggacgtcc atattaggac gtccatatta ggacgtccat attaggacgt ccatattagg     180
acgtccatat taggacgtcc atattaggac gtccatatta ggacgtccat attaggacgt     240
ccatattagg acgtccatat taggacgtcc atattaggac                           280
```

```
<210> SEQ ID NO 23
<211> LENGTH: 800
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(800)
<223> OTHER INFORMATION: This sequence may encompass 2-16 or 20
      "TCTCAATCCACAAT-CTCGGAGTATGTCTAGACTGACAATG" repeating units
<220> FEATURE:
<223> OTHER INFORMATION: See specification as filed for detailed
      description of substitutions and preferred embodiments

<400> SEQUENCE: 23
tctcaatcca caatctcgga gtatgtctag actgacaatg tctcaatcca caatctcgga      60
gtatgtctag actgacaatg tctcaatcca caatctcgga gtatgtctag actgacaatg     120
tctcaatcca caatctcgga gtatgtctag actgacaatg tctcaatcca caatctcgga     180
gtatgtctag actgacaatg tctcaatcca caatctcgga gtatgtctag actgacaatg     240
tctcaatcca caatctcgga gtatgtctag actgacaatg tctcaatcca caatctcgga     300
gtatgtctag actgacaatg tctcaatcca caatctcgga gtatgtctag actgacaatg     360
tctcaatcca caatctcgga gtatgtctag actgacaatg tctcaatcca caatctcgga     420
gtatgtctag actgacaatg tctcaatcca caatctcgga gtatgtctag actgacaatg     480
tctcaatcca caatctcgga gtatgtctag actgacaatg tctcaatcca caatctcgga     540
gtatgtctag actgacaatg tctcaatcca caatctcgga gtatgtctag actgacaatg     600
tctcaatcca caatctcgga gtatgtctag actgacaatg tctcaatcca caatctcgga     660
gtatgtctag actgacaatg tctcaatcca caatctcgga gtatgtctag actgacaatg     720
tctcaatcca caatctcgga gtatgtctag actgacaatg tctcaatcca caatctcgga     780
gtatgtctag actgacaatg                                                 800

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Asp Asp Lys
1               5

<210> SEQ ID NO 26
<211> LENGTH: 168
<212> TYPE: PRT
<213> ORGANISM: Artificial Sequence
```

```
<220> FEATURE:
<223> OTHER INFORMATION: Description of Artificial Sequence: Synthetic
      consensus polypeptide

<400> SEQUENCE: 26

Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
                20                  25                  30

Lys Lys Leu Pro Leu Glu Val Leu Lys Glu Ile Glu Ala Asn Ala Arg
            35                  40                  45

Lys Ala Gly Cys Thr Arg Gly Cys Leu Ile Cys Leu Ser His Ile Lys
        50                  55                  60

Cys Thr Pro Lys Met Lys Lys Phe Ile Pro Gly Arg Cys His Thr Tyr
65                  70                  75                  80

Glu Gly Asp Lys Glu Ser Ala Gln Gly Gly Ile Gly Glu Ala Ile Val
                85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
            115                 120                 125

Lys Gly Leu Ala Asn Val Gln Cys Ser Asp Leu Leu Lys Lys Trp Leu
        130                 135                 140

Pro Gln Arg Cys Ala Thr Phe Ala Ser Lys Ile Gln Gly Gln Val Asp
145                 150                 155                 160

Lys Ile Lys Gly Ala Gly Gly Asp
                165
```